US012663830B2

(12) United States Patent
Cui et al.

(10) Patent No.: US 12,663,830 B2
(45) Date of Patent: Jun. 23, 2026

(54) ARTIFICIAL INTELLIGENCE (AI) / MACHINE LEARNING (ML) ENABLED ADAPTIVE/CONFIGURABLE INTERNET-OF-THINGS (IoT) SERVICES

(71) Applicant: AT&T Intellectual Property I, L.P., Atlanta, GA (US)

(72) Inventors: Zhi Cui, Sugar Hill, GA (US); Paul Edward Smith, Jr., Heath, TX (US); Venson Shaw, Kirkland, WA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 171 days.

(21) Appl. No.: 18/594,048

(22) Filed: Mar. 4, 2024

(65) Prior Publication Data

US 2025/0278115 A1 Sep. 4, 2025

(51) Int. Cl.
*G06F 1/16* (2006.01)
*G06F 3/01* (2006.01)
*G16H 10/60* (2018.01)

(52) U.S. Cl.
CPC .............. *G06F 1/163* (2013.01); *G06F 3/011* (2013.01); *G16H 10/60* (2018.01)

(58) Field of Classification Search
CPC .......... G06F 1/163; G06F 3/011; G16H 10/60
See application file for complete search history.

(56) References Cited

U.S. PATENT DOCUMENTS

2023/0045403 A1* 2/2023 Robison .............. A61B 5/4848
2024/0095100 A1* 3/2024 Pateromichelakis ... G06F 9/541

FOREIGN PATENT DOCUMENTS

CN 209285861 U * 8/2019

* cited by examiner

*Primary Examiner* — Haoshian Shih
(74) *Attorney, Agent, or Firm* — Guntin & Gust, PLC; Kenneth S. Kwan

(57) ABSTRACT

Aspects of the subject disclosure may include, for example, obtaining sensor data relating to a body part of a user, determining one or more adjustments to a shape or a structure of the device based on the sensor data, resulting in one or more determined adjustments, and causing the one or more determined adjustments to be made to the shape or the structure of the device, thereby providing for dynamic reconfiguration of the device for facilitating user treatment. Other embodiments are disclosed.

20 Claims, 9 Drawing Sheets

280

200

270

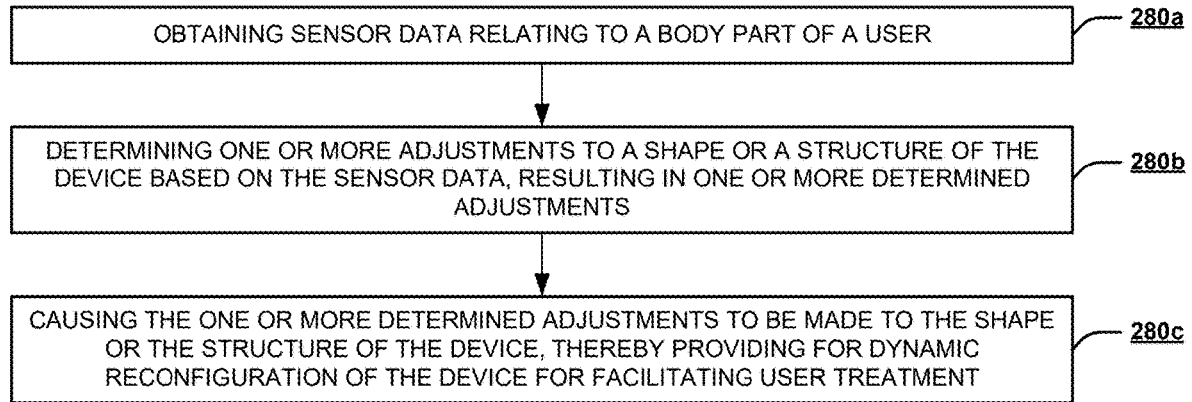

OBTAINING SENSOR DATA RELATING TO A BODY PART OF A USER — 280a

DETERMINING ONE OR MORE ADJUSTMENTS TO A SHAPE OR A STRUCTURE OF THE DEVICE BASED ON THE SENSOR DATA, RESULTING IN ONE OR MORE DETERMINED ADJUSTMENTS — 280b

CAUSING THE ONE OR MORE DETERMINED ADJUSTMENTS TO BE MADE TO THE SHAPE OR THE STRUCTURE OF THE DEVICE, THEREBY PROVIDING FOR DYNAMIC RECONFIGURATION OF THE DEVICE FOR FACILITATING USER TREATMENT — 280c

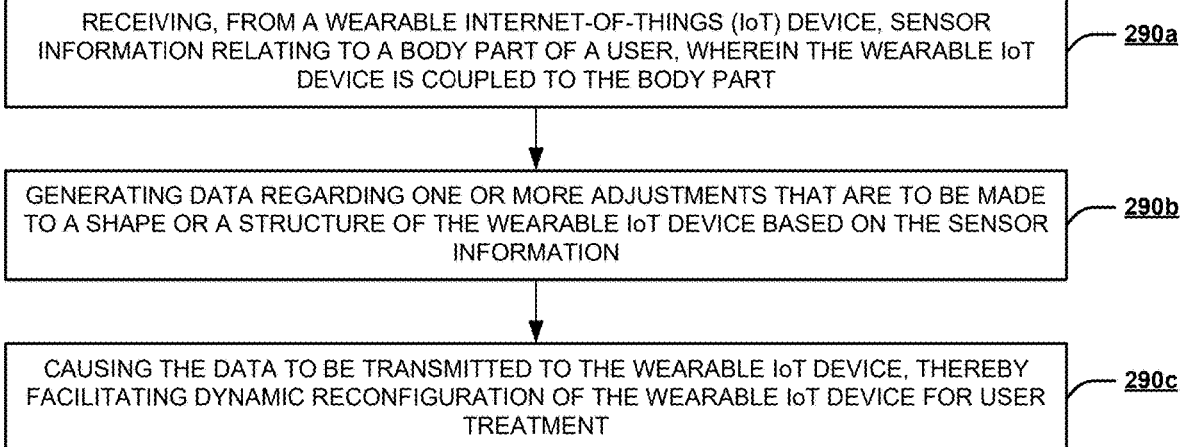

RECEIVING, FROM A WEARABLE INTERNET-OF-THINGS (IoT) DEVICE, SENSOR INFORMATION RELATING TO A BODY PART OF A USER, WHEREIN THE WEARABLE IoT DEVICE IS COUPLED TO THE BODY PART — 290a

GENERATING DATA REGARDING ONE OR MORE ADJUSTMENTS THAT ARE TO BE MADE TO A SHAPE OR A STRUCTURE OF THE WEARABLE IoT DEVICE BASED ON THE SENSOR INFORMATION — 290b

CAUSING THE DATA TO BE TRANSMITTED TO THE WEARABLE IoT DEVICE, THEREBY FACILITATING DYNAMIC RECONFIGURATION OF THE WEARABLE IoT DEVICE FOR USER TREATMENT — 290c

ARTIFICIAL INTELLIGENCE (AI) / MACHINE LEARNING (ML) ENABLED ADAPTIVE/CONFIGURABLE INTERNET-OF-THINGS (IoT) SERVICES

FIELD OF THE DISCLOSURE

The subject disclosure relates to artificial intelligence (AI)-/machine learning (ML)-enabled adaptive/configurable Internet-of-Things (IoT) services for wearable IoT devices.

BACKGROUND

Traditional patient therapy and treatments are generally performed at the office using specialized equipment. Certain supporting or stabilizing devices, such as shoe inserts, braces, and the like can also be customized and worn by the user during work or in the home.

BRIEF DESCRIPTION OF THE DRAWINGS

Reference will now be made to the accompanying drawings, which are not necessarily drawn to scale, and wherein:

FIG. 2C depicts an illustrative embodiment of a method in accordance with various aspects described herein.

FIG. 2D depicts an illustrative embodiment of a method in accordance with various aspects described herein.

DETAILED DESCRIPTION

Figure 1:
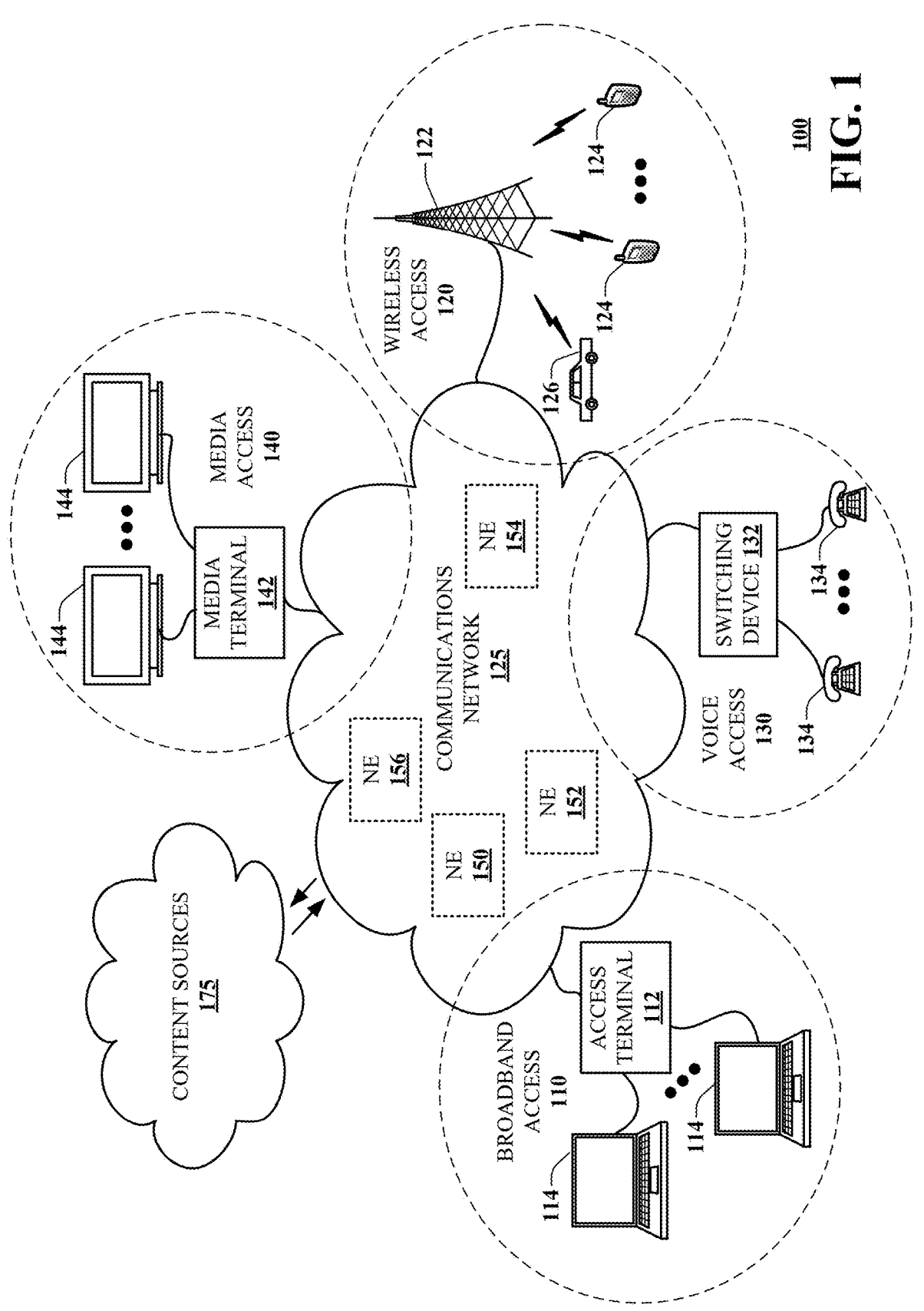
FIG. 1 is a block diagram illustrating an exemplary, non-limiting embodiment of a communications network in accordance with various aspects described herein.

With improving technology, more advanced wearable devices are being developed to help assist patients with recovery and maintenance. These include a variety of equipment that can be worn on a body part, such as shoes, shoes inserts, shirts, hats, gloves, braces, and more.

The subject disclosure describes, among other things, illustrative embodiments of a system that facilitates AI-/ML-enabled adaptive/configurable IoT services for wearable IoT devices. A wearable IoT device may be capable of monitoring conditions associated with a user, such as conditions relating to one or more corresponding body parts of the user, and may be capable of deriving or obtaining treatment instructions/recommendations for real-time (or near real-time) adjustments to the shape or structure of the device based on the monitoring. In various embodiments, the wearable IoT device may be configured with one or more sensors for monitoring the conditions, and one or more structural components for making the adjustments. For instance, a reconfigurable insert for placement in a shoe may be configured with sensors for monitoring the conditions associated with a user's foot (e.g., pressure, weight, strength/weakness, etc.), and built-in electromechanical component(s) for adaptively adjusting the shape or structure of the insert so as to correct the position/pressure of the foot for pain prevention or management. As another example, an adaptive shirt may be equipped with sensors for monitoring the conditions associated with a user's shoulders or back (e.g., pressure, weight, strength/weakness, lifting of a heavy object, etc.), and built-in electromechanical component(s) for automatically adjusting the shape or structure of the shirt so as to support the position of the shoulder or the back for injury prevention.

In some embodiments, the wearable IoT device may be equipped with AI/ML functionality that is trained to generate treatment instructions or refinements (i.e., commands to the adjustable components) based on sensor data. In certain embodiments, the wearable IoT device may make adjustments to the device's shape/structure not only based on monitored user activity/posture but also in accordance with learnings associated with the treatment/progress of other users. These learnings may be obtained from a (e.g., cloud-based) adaptive/configurable IoT system that facilitates (e.g., optimal) reconfiguration of wearable IoT devices.

In one or more embodiments, the adaptive/configurable IoT system may be configured to implement some or all of the aforementioned instruction generation functionality, and provide treatment instructions/recommendations to wearable IoT devices by way of a network. The network may be architected to facilitate real-time (or near real-time) delivery of services to wearable IoT devices. The network may be implemented based on 5G technology, 6G technology, or a higher generation network technology. In one or more embodiments, the network may be configured to employ network slicing for efficient allocation of network resources that meet requirements associated with the IoT service, and may provide for IoT service-based policy management and charging. In certain embodiments, the adaptive/configurable IoT system may be configured to obtain or collect sensor data from a wearable IoT device, train one or more AI/ML models based on treatments associated with a user of the device and/or based on treatments associated with users of other devices, and use such model(s) to generate treatment instructions/recommendations. In one or more embodiments, the adaptive/configurable IoT system may make collected data, treatment instructions/recommendations, and/or treatment results accessible to health service providers (e.g., physicians, physical therapists, etc.) for review. In various embodiments, the adaptive/configurable IoT system may provide treatment instructions/recommendations to wearable IoT devices via a base station and/or via one or more mobile edge computing (MEC) devices. For instance, the adaptive/configurable IoT system may be included in (and/or distributed across) one or more MEC devices, which may be implemented at a network edge, one or more central offices, one or more hubs, one or more cell sites (such as one or more radio access network devices), one or more routing devices, or the like. These embodiments enable faster delivery of treatment instructions/recommendations to wearable IoT devices.

Embodiments of the wearable IoT device and IoT service delivery network architecture, described herein, revolutionize patient treatment and therapy by enabling active, adaptive and real-time reconfiguration or adjustments of wearables, which advantageously improves end user health and experience. This also extends the use of AI/ML in a multi-dimensional manner, allowing an AI/ML system to be more user-definable, device-definable, and/or service-definable.

One or more aspects of the subject disclosure include a device, comprising a processing system including a processor, and a memory that stores executable instructions that, when executed by the processing system, facilitate performance of operations. The operations can include obtaining sensor data relating to a body part of a user. Further, the operations can include determining one or more adjustments to a shape or a structure of the device based on the sensor data, resulting in one or more determined adjustments. Further, the operations can include causing the one or more determined adjustments to be made to the shape or the structure of the device, thereby providing for dynamic reconfiguration of the device for facilitating user treatment.

One or more aspects of the subject disclosure include a non-transitory machine-readable medium, comprising executable instructions that, when executed by a processing system including a processor, facilitate performance of operations. The operations can include receiving, from a wearable Internet-Of-Things (IoT) device, sensor information relating to a body part of a user, wherein the wearable IoT device is coupled to the body part. Further, the operations can include generating data regarding one or more adjustments that are to be made to a shape or a structure of the wearable IoT device based on the sensor information. Further, the operations can include causing the data to be transmitted to the wearable IoT device, thereby facilitating dynamic reconfiguration of the wearable IoT device for user treatment.

One or more aspects of the subject disclosure include a method. The method can comprise obtaining, by a processing system of a wearable Internet-Of-Things (IoT) device including a processor, sensor data relating to one or more body parts of a user. Further, the method can include determining, by the processing system, one or more adjustments to a shape or a structure of the wearable IoT device based on the sensor data, resulting in one or more determined adjustments. Further, the method can include causing, by the processing system, the one or more determined adjustments to be made to the shape or the structure of the wearable IoT device, thereby providing for dynamic reconfiguration of the wearable IoT device for facilitating user treatment of the one or more body parts.

Other embodiments are described in the subject disclosure.

Referring now to FIG. 1, a block diagram is shown illustrating an example, non-limiting embodiment of a system 100 in accordance with various aspects described herein. For example, system 100 can facilitate, in whole or in part, AI-/ML-enabled adaptive/configurable IoT services for a wearable IoT device. In particular, a communications network 125 is presented for providing broadband access 110 to a plurality of data terminals 114 via access terminal 112, wireless access 120 to a plurality of mobile devices 124 and vehicle 126 via base station or access point 122, voice access 130 to a plurality of telephony devices 134, via switching device 132 and/or media access 140 to a plurality of audio/video display devices 144 via media terminal 142. In addition, communications network 125 is coupled to one or more content sources 175 of audio, video, graphics, text and/or other media. While broadband access 110, wireless access 120, voice access 130 and media access 140 are shown separately, one or more of these forms of access can be combined to provide multiple access services to a single client device (e.g., mobile devices 124 can receive media content via media terminal 142, data terminal 114 can be provided voice access via switching device 132, and so on).

The communications network 125 includes a plurality of network elements (NE) 150, 152, 154, 156, etc. for facilitating the broadband access 110, wireless access 120, voice access 130, media access 140 and/or the distribution of content from content sources 175. The communications network 125 can include a circuit switched or packet switched network, a voice over Internet protocol (VOIP) network, Internet protocol (IP) network, a cable network, a passive or active optical network, a 4G, 5G, or higher generation wireless access network, WIMAX network, UltraWideband network, personal area network or other wireless access network, a broadcast satellite network and/or another communications network.

In various embodiments, the access terminal 112 can include a digital subscriber line access multiplexer (DSLAM), cable modem termination system (CMTS), optical line terminal (OLT) and/or other access terminal. The data terminals 114 can include personal computers, laptop computers, netbook computers, tablets or other computing devices along with digital subscriber line (DSL) modems, data over coax service interface specification (DOCSIS) modems or other cable modems, a wireless modem such as a 4G, 5G, or higher generation modem, an optical modem and/or other access devices.

In various embodiments, the base station or access point 122 can include a 4G, 5G, or higher generation base station, an access point that operates via an 802.11 standard such as 802.11n, 802.11ac or other wireless access terminal. The mobile devices 124 can include mobile phones, e-readers, tablets, phablets, wireless modems, and/or other mobile computing devices.

In various embodiments, the switching device 132 can include a private branch exchange or central office switch, a media services gateway, VoIP gateway or other gateway device and/or other switching device. The telephony devices 134 can include traditional telephones (with or without a terminal adapter), VoIP telephones and/or other telephony devices.

In various embodiments, the media terminal 142 can include a cable head-end or other TV head-end, a satellite receiver, gateway or other media terminal 142. The display devices 144 can include televisions with or without a set top box, personal computers and/or other display devices.

In various embodiments, the content sources 175 include broadcast television and radio sources, video on demand platforms and streaming video and audio services platforms, one or more content data networks, data servers, web servers and other content servers, and/or other sources of media.

In various embodiments, the communications network 125 can include wired, optical and/or wireless links and the network elements 150, 152, 154, 156, etc. can include service switching points, signal transfer points, service control points, network gateways, media distribution hubs, servers, firewalls, routers, edge devices, switches and other network nodes for routing and controlling communications traffic over wired, optical and wireless links as part of the Internet and other public networks as well as one or more private networks, for managing subscriber access, for billing and network management and for supporting other network functions.

Figure 2A:
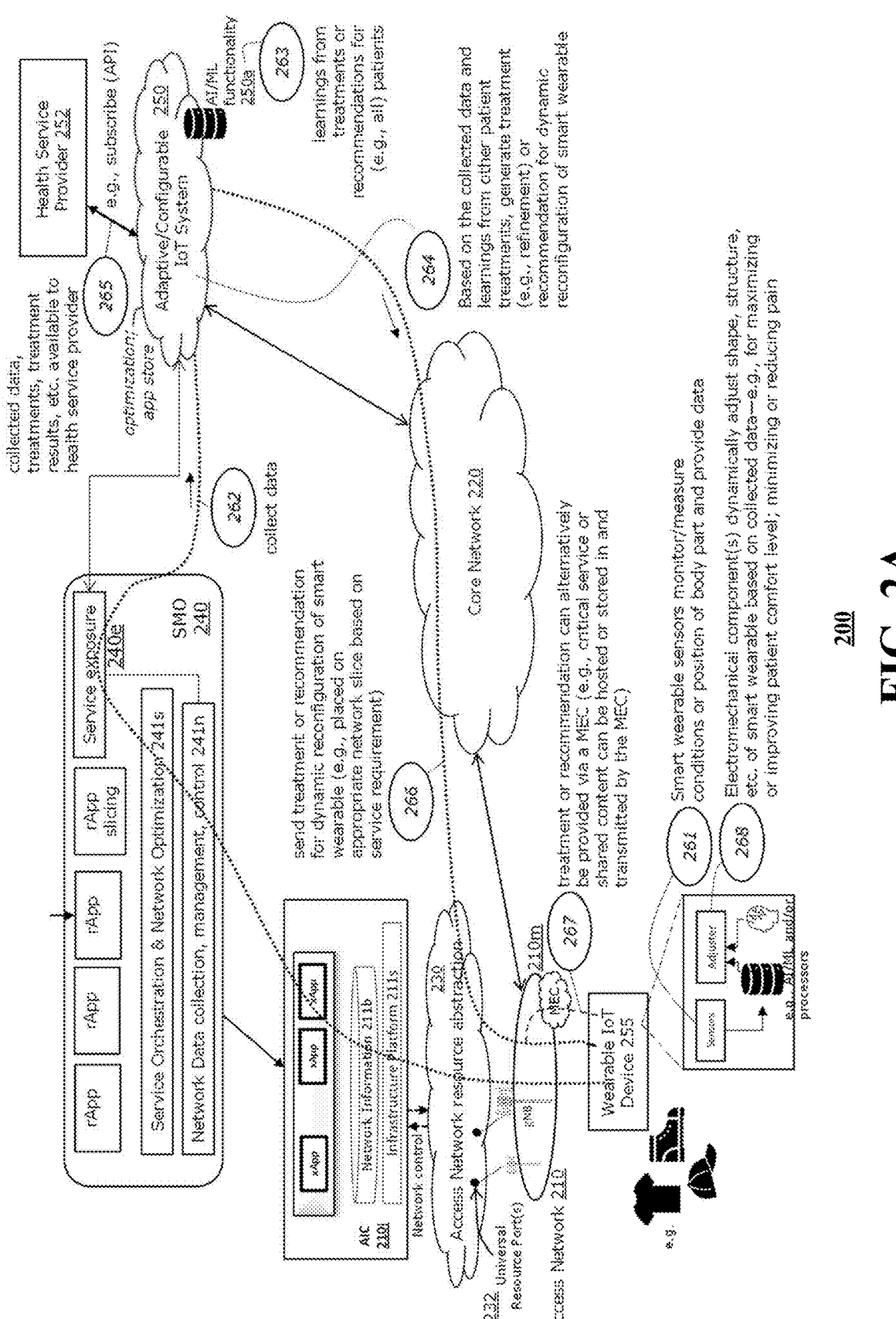
FIG. 2A is a block diagram illustrating an example, non-limiting embodiment of a system functioning within, or operatively overlaid upon, the communications network of FIG. 1 in accordance with various aspects described herein.

FIG. 2A is a block diagram illustrating an example, non-limiting embodiment of a network architecture of a system 200 (e.g., a network system 200) functioning within, or operatively overlaid upon, the communications network 100 of FIG. 1 in accordance with various aspects described herein. As shown in FIG. 2A, the network system 200 may include an access network 210 (e.g., wireless radio access network(s) (RAN(s)), Wi-Fi network(s), and/or wireline network(s)), a core network 220, an access network intelligent controller (AIC) 210*i*, a service management and orchestration system (SMO) 240, an adaptive/configurable IoT system 250, and wearable IoT device(s) 255. As described in more detail below, the access network 210, the core network 220, the AIC 210*i*, the SMO 240, and the adaptive/configurable IoT system 250 may interact with one another to facilitate the provision of AI/ML enabled services to wearable IoT device(s) 255.

A wearable IoT device 255 can be an adaptive or reconfigurable object such as, for instance, a shoe, a shoe insert, a sock, a shirt, a vest, a jacket, a pair of pants, a scarf, a hat, a mask, a wristwatch, a headband, a wristband, a knee brace, a glove, a headset, headphones, glasses, goggles, a similar type of device, any other device that can be worn or coupled to a body part of user (e.g., person or animal), any similar device, or a combination of some or all of these devices. Wearable IoT device 255 can be equipped with one or more transmitter (Tx) devices and/or one or more receiver (Rx) devices configured to communicate with, and utilize network resources of, the network system 200. In exemplary embodiments, wearable IoT device 255 may be equipped with one or more sensors for monitoring conditions and/or the position associated with a body part. In one or more embodiments, wearable IoT device 255 may be equipped with one or more processors and/or AI/ML functionality for dynamically determining adjustments that should be made to the shape/structure of the wearable IoT device 255 based on the sensor data, and one or more (e.g., electrical, mechanical, electromechanical, etc.) components for effecting those adjustments. As an example, in a case where the wearable IoT device 255 is a shoe or a shoe insert, one or more sensors thereof may monitor movement, posture, pressure, weight, strength/weakness, or any other parameter associated with a foot, one or more processors and/or AI/ML functionality thereof may dynamically determine adjustments that should be made to the shape/structure of the device, and one or more adjustable components therefor may effect such adjustments. As another example, in a case where the wearable IoT device 255 is a shirt, a vest, a jacket, or the like, one or more sensors thereof may monitor movement, posture, pressure, weight, strength/weakness, or any other parameter associated with the chest, back, abdomen, neck, etc., one or more processors and/or AI/ML functionality thereof may dynamically determine adjustments that should be made to the shape/structure of the device, and one or more adjustable components therefor may effect such adjustments.

The access network 210 may include network resources, such as one or more physical resources (or network nodes) and/or one or more logical resources. The physical resources may include base station(s), such as one or more gNodeBs (gNBs) or the like. In various embodiments, the physical resources may additionally, or alternatively, include one or more satellites and/or uncrewed aerial vehicles (UAVs), one or more Gigabyte Passive Optical Networks (GPONs) and/or related components (e.g., Optical Line Terminal(s) (OLT), Optical Network Unit(s) (ONU), etc.), and/or the like. A base station may employ any suitable radio access technology (RAT), such as 5G, 6G, or any higher generation RAT. The logical resources may include a voice service system (e.g., a hardware and/or software implementation of voice-related functions), a video service system (e.g., a hardware and/or software implementation of video-related functions, such as coder-decoder or compression-decompression (CO-DEC) components or the like), a security service system (e.g., a hardware and/or software implementation of security-related functions), and/or the like. The access network 210 may be in communication with the core network 220 via intermediate links provided by a backhaul or transport network (not shown). In various embodiments, the transport network may include a mobile network or backhaul that is fiber-based and/or that is implemented via wireless point-to-point technologies. In certain embodiments, the transport network may additionally, or alternatively, be implemented using copper wireline, satellite communications technologies, and/or point-to-multipoint wireless technologies.

In one or more embodiments, the network system 200 may include one or more edge systems. An edge system may include MEC network(s) and compute device(s) 210*m*, which may be useful in reducing (e.g., minimizing) delays associated with provisioning of data or services to one or more (requesting) devices located proximate to (e.g., within a threshold distance from) a corresponding base station. In various embodiments, one or more of the edge systems may include a MEC Hub device and compute device(s) communicatively coupled to the MEC Hub device that function as controller(s) in respective heterogeneous cells. In certain embodiments, one or more of the MEC Hub device and/or the compute devices can additionally, or alternatively, function as a controller for non-terrestrial cells. In some embodiments, a MEC Hub device and compute devices can be communicatively coupled to one another via an interface, such as a wired and/or wireless interface (e.g., fiber cable(s), hybrid fiber coaxial (HFC) cable(s), or the like). In some embodiments, a MEC Hub device can function as a centralized MEC node for the various cells.

In various embodiments, one or more (e.g., each) of the edge systems (e.g., a MEC Hub device and/or compute devices) can manage an inventory of associated base stations, and can store data relating to such base stations in a data structure (e.g., a database, an array, a linked list, a table, a tree, and/or the like). The data relating to a base station can include, for example, information regarding an identity of the base station (e.g., a physical cell identifier (PCI) or the like), a location of the base station, actual or estimated available bandwidth of the base station, throughput of the base station, etc. In various embodiments, for example, a MEC Hub device and/or compute devices can dynamically update entries in the data structure in real-time, or near real-time, as updated data relating to the associated base station is received.

In various embodiments, an edge system (e.g., a MEC Hub device and/or computing devices) can be controlled to obtain and store data relating to wearable IoT device(s) 255. Such data may include information regarding the device's current shape or structure (e.g., orientations, relative angular positions, etc. of adjustable components thereof), information regarding an identity of the device, a current location of the device, current signal strength(s) of nearby access points as measured by the device, a direction of movement of the device, a speed of travel of the device, physical layer properties of the device, signal round trip times (RTT), etc. In various embodiments, a MEC Hub device and/or computing devices can be dynamically updated in real-time, or near real-time, as changes relating to a wearable IoT device 255 are detected.

Although not shown, in exemplary embodiments, the network system 200 may include any number of edge systems/devices associated with base stations of the access network 210. In various embodiments, the base stations and corresponding edge systems may be associated with (e.g., respective) cells, such as heterogeneous cells (e.g., that provide access to the network system 200 using different types of RATs). In various embodiments, the cells can be terrestrial cells (e.g., one or more macrocells, small cells or microcells, Wi-Fi-based cell(s), or the like) or non-terrestrial cells (e.g., a flying cell, or drone cell, served by UAVs). The network system 200 can include various quantities of cells (e.g., primary cells and/or secondary cells), various quantities of base stations in a cell, and/or various types of base stations and/or cells. Wearable IoT device(s) 255 can be located within cell coverage areas of the network system 200, provided by cells associated with the base stations, and may travel amongst various ones of the cells.

The core network 220 may include various network devices and/or systems that provide a variety of functions. Examples of functions provided by, or included, in the core network 220 include an access mobility and management function (AMF) configured to facilitate mobility management in a control plane of the network system 200, a User Plane Function (UPF) configured to provide access to a data network (such as a packet data network (PDN) in a user (or data) plane of the network system 200), a Unified Data Management (UDM) function, a Session Management Function (SMF), a Policy Control Function (PCF), and/or the like. In one or more embodiments, the core network 220 may include a 5G core (5GC) (associated with an SMF), a 6G core (6GC) (associated with a control plane function (CPF)), and/or a Broadband Network Gateway (BNG). In various embodiments, the core network 220 may include one or more devices implementing other functions, such as a master user database server device for network access management, a PDN gateway server device for facilitating access to a PDN, and/or the like. The core network 220 may be in further communication with one or more other networks (e.g., one or more content delivery networks (CDNs)), one or more services, and/or one or more devices. In one or more embodiments, the core network 220 may be implemented in distributed cores.

As shown in FIG. 2A, the network system 200 may include an access network resource abstraction layer or system 230. In exemplary embodiments, the access network resource abstraction layer or system 230 may provide abstractions of the physical resources and/or logical resources. In various embodiments, the physical resources and the logical resources may be abstracted and be accessible via universal resource ports 232. In one or more embodiments, the abstractions may be from Layer 2 (e.g., Ethernet or data link layer) and above in the Open Systems Interconnection (OSI) Model. Such abstractions allow the physical resources and the logical resources to be presented to the SMO 240 as universal resources (e.g., similar to plug-ins with a universal interface, such as the Universal Serial Bus (USB)), which can enable the SMO 240 to access and leverage the universal resources to provide or support IoT-related services. In this way, for example, access, control, and usage of the physical resources and the logical resources of the access network 210 may be all based on software from Layer 2 and above.

Example implementations of the universal resource ports 232 and the access network resource abstraction are described in U.S. patent application Ser. No. 17/846,087 filed on Jun. 22, 2022, entitled "METAVERSE END-TO-END (E2E) NETWORK ARCHITECTURE," which is incorporated by reference herein in its entirety. Providing network resource abstractions enables a system, such as SMO 240 to (e.g., optimally) select, and connect, cost-effective features or resources (e.g., access network resources, transport network resources, core network resources, etc.) to meet IoT service needs.

As depicted, the AIC 210*i* may interface the SMO 240 and the access network 210. In various embodiments, the AIC 210*i* may be capable of providing real-time (or near real-time) microservices associated with the access network 210, and may be leveraged to select the most appropriate access technology or technologies that meet the needs of IoT services. As shown, the AIC 210*i* may include an infrastructure platform 211*s*, a network information database 211*b*, and various applications (xApps). The infrastructure platform 211*s* may provide control functions for managing or providing microservices relating to wireline-based network resources and wireless-based network resources. The network information database 211*b* may store information regarding the various wireline-based network resources and wireless-based network resources, load conditions associated with those resources, availability of those resources, and/or the like. In exemplary embodiments, the AIC 210*i* may be similar to a RAN intelligent controller (RIC), but may include functionality for managing wireline-based network resources as well as wireless-based network resources. In this sense, the AIC 210*i* may thus operate as a "general" access network controller.

Although not shown, in certain embodiments, portion(s) of the access network 210 may be, or may include, a virtual RAN (vRAN) (e.g., in an open-RAN (O-RAN) implementation) in which software is decoupled from hardware and implementation thereof is in accordance with principles of network function virtualization (NFV), where the control plane is separated from the data plane. In these embodiments, the vRAN may include a centralized set of baseband units located remotely from antennas and remote radio units, may be configured to share signaling amongst cells, and may provide control and service delivery optimization functions. Here, the AIC 210*i* may include a network service management platform and RIC functionality (e.g., implemented in the infrastructure platform 211*s*). For instance, the AIC 210*i* may include a first RIC portion that is implemented, or otherwise incorporated, in the network service management platform, and may also include a second RIC portion having a centralized unit (CU) (e.g., a base station CU, such as a gNB CU or the like) that provides a CU applications layer as well as a CU control plane CU-CP and a CU user plane CU-UP. The particular functions performed by the two RIC portions can vary based on various criteria, including requirements of the network, and can also include redundancy and/or dynamic switching of functions (including functions described herein) between the two RIC portions. Additionally, the vRAN may include distributed units (DUs)—i.e., baseband units (e.g., base station DUs, such as gNB DUs or the like) configured to perform signal processing, UE scheduling, and/or the like, where each of DUs may be implemented as a virtual DU (vDU). Further, the vRAN may also include remote radio heads or remote units (RUs) for communicative coupling (e.g., via an air interface) with wearable IoT device(s) 255. The RUs, the DUs, and the CU may, by way of a fronthaul (e.g., having open standards, such as O-RAN standards or the like), a midhaul, and a backhaul (e.g., portion(s) of transport network(s)), provide (e.g., controlled) connectivity between wearable IoT device(s) 255 and (e.g., portion(s) of) the core network 220. The network service management platform and/or the first RIC portion may be operative at or in non-real-time; the second RIC portion and/or the CU may be operative at or in near-real-time; and the DUs, the RUs, and/or wearable IoT device(s) 255 may be operative at or in real-time. As the terms (and related terms) are used herein, real-time operations may occur over a span of fractions of a second up to a second (or the like), near-real-time operations may occur over the course of a few seconds (e.g., 1 to 5 seconds or the like), and non-real-time operations may occur over a time period that is greater than a few seconds (e.g., greater than 5 seconds or the like). The network service management platform may manage, or otherwise adapt, RIC behaviors and/or operations across one or more of the three time zones or timeframes described above (e.g., real-time, near-real-time, and non-real-time) on an individualized and/or collective basis. Such management or adaptation of RIC behaviors and/or operations may conform to one or more models or microservices (e.g., AI models or microservices). In turn, the RIC portions may establish and/or modify policies and/or behaviors of respective CUs, DUs, and RUs in accordance with the model(s) or microservice(s). In this regard, the network service management platform may indirectly influence the behaviors and/or operations of CUs, DUs, and/or RUs via one or more of the RIC portions. The communication channels and/or links between the vRAN and wearable IoT device(s) 255 may include wireless links. For example, some or all of the wearable IoT device(s) 255 may be mobile, and may therefore enter and/or exit a service or coverage area associated with the vRAN. Also, some of the wearable IoT device(s) 255 may include non-mobile or stationary devices. The vRAN may thus include one or more routers, gateways, modems, cables, wires, and/or the like, and the communication channels and/or links between the vRAN and the non-mobile or stationary wearable IoT device(s) 255 may include wired/wireline links, optical links, etc. In certain embodiments, the second RIC portion may store, execute, and/or deploy in or via an applications layer (e.g., the aforementioned CU applications layer), applications or microservices (e.g., xApps or the like) that are configured to control and manage the vRAN. The applications or microservices may relate to scheduler capacity optimization, coverage optimization, capacity optimization (including, for example, via interference mitigation), user quality optimization (including, for example, for an uplink (UL) and/or a downlink (DL)), radio connection management, mobility management, quality-of-service (QoS) management, interference management, and/or the like. One or more of the RIC portions may also be configured to execute, or otherwise deploy, models, such as AI (e.g., ML) models that, when executed in one or more containers, provide corresponding microservices. Deployment of a microservice, such as an AI model or microservice, in the RIC portion(s) may involve, or include, for example, executing or instantiating the AI model in one or more containers in the applications layer of the RIC (e.g., the aforementioned CU applications layer), such that the AI model processes inputs (e.g., received from other microservices running on the RIC and/or from various components of the vRAN, such as the CU-CP & CU-UP, the DUs, and/or the RUs) and provides outputs (e.g., to the other microservices and/or the various components of the vRAN), in accordance with the AI model, to control the overall operation of the vRAN. Examples of microservices provided by AI model(s) can include those relating to scheduler capacity optimization, coverage optimization, capacity optimization (including, for example, via interference mitigation), user quality optimization (including, for example, for the UL and/or the DL), telemetry, network traffic control and/or management, device admissions (e.g., UE admissions control), and/or the like.

The SMO 240 may be configured to manage and orchestrate network services for efficient and/or optimal performance and resource utilization. In various embodiments, the SMO 240 may include service orchestration and network optimization functionality 241s, which may facilitate configuration, coordination, and/or management of network services in accordance with service requirements, service provisioning, scaling, and/or decommissioning, load balancing, Quality of Service (QOS) management, and/or routing optimization. In one or more embodiments, the SMO 240 may include network data collection, management, control functionality 241n, which may facilitate collection of data from various network elements and devices (e.g., that inform on network performance, resource utilization patterns, etc.), configuration management, policy enforcement, and/or fault detection. In certain embodiments, the SMO 240 may include one or more rApps (including those capable of facilitating network slicing) that are configured to facilitate usage of network resources based on network conditions. In exemplary embodiments, one or more functionalities in the SMO 240 may be capable of communicating with the AIC 210i (e.g., via application programming interface (API) calls or the like) to obtain data regarding (e.g., the availability and the load conditions of) the resources in the access network 210 and/or the core network 220. In one or more embodiments, the functionalities may be capable of polling the AIC 210i and/or the core network 220 for the necessary data or may be notified of state changes or updates (e.g., based on load condition(s) or resource availability satisfying threshold(s)). As shown in FIG. 2A, the SMO 240 may include service exposure functionality 240e that coordinates service instantiation and service/network resource chaining to meet the needs of IoT services.

In one or more embodiments, the SMO 240 may allow the network system 200 to separate control plane operations from data plane operations, and may enable layer abstraction for separating service and network functions or elements from physical network functions or elements. In various embodiments, the SMO 240 may be communicatively coupled with a backend system (e.g., a backend customer service portal or the like) via which external systems (e.g., health service provider systems or devices) may submit IoT service request(s) associated with users or devices (e.g., wearable IoT device(s) 255).

In exemplary embodiments, the SMO 240 may be capable of performing service design and orchestration based on received IoT service requests. The SMO 240 may analyze an IoT service request to determine functions and/or network data flows that are needed to facilitate delivery of the requested IoT service. In various embodiments, the SMO 240 may select/define a directed graph and/or an associated model that identifies features of the requested IoT service. The SMO 240 may generate IoT service model(s) for the requested IoT service in a programming language or format, such as Extensible Markup Language (XML), Yang models, other types of files, combinations thereof, or the like.

In one or more embodiments, the SMO 240 may effect service creation/selection and composition of resources to satisfy the needs of a requested IoT service. In certain embodiments, the SMO 240 may design the chain of resources based on those needs. In this way, the SMO 240 may, with access to resource abstractions and based on requested IoT service requirements, design and orchestrate IoT service delivery for end consumers using the most cost-effective resources across the access network 210 and the core network 220. In some embodiments, the SMO 240 may also determine, and use, information regarding associated user priorities, extant network resource loadings, and/or the like to compose a requested IoT service. In various embodiments, the SMO 240 may dynamically alter chains based on detected changes (or trigger conditions), such as a change in a physical location of a wearable IoT device 255, a change to interface equipment, and so on. Some or all of these changes may be detected by the AIC 210i and reported to the SMO 240 for any necessary responsive actions (e.g., shown as "network control" in FIG. 2A).

In exemplary embodiments, the SMO 240 may derive (or stitch together) a designed IoT service path. In various embodiments, the SMO 240 may configure policies associated with an endpoint device (e.g., a wearable IoT device 255 associated with a user), and may instantiate a route (or connection) between the selected universal resource ports to establish the networking between the selected universal resource ports so as to configure, or otherwise set up, the connections for IoT service delivery. For example, the route may run between the selected universal resource ports across the access network 210 and/or the core network 220 to the adaptive/configurable IoT system 250.

In this way, the SMO 240 may coordinate with one or more of the AIC 210i and the core network 220 to ascertain the availability, status, and/or requirements of the portfolios of resources in the underlying networks and effect dynamic, intelligent composition of IoT service functions and associated interfaces (by instantiating routes and logical ports across the access network 210 and/or the core network 220) to derive an IoT service instance for a requested IoT service.

The adaptive/configurable IT system 250 may be implemented in one or more servers for interfacing the network architecture with AI/ML capabilities. In exemplary embodiments, the adaptive/configurable IoT system 250m may include or have access to AI/ML functionality 250a for training model(s) that identify suitable adjustments to the shape/structure of a wearable IoT device 255 based on sensor data.

Figure 2B:
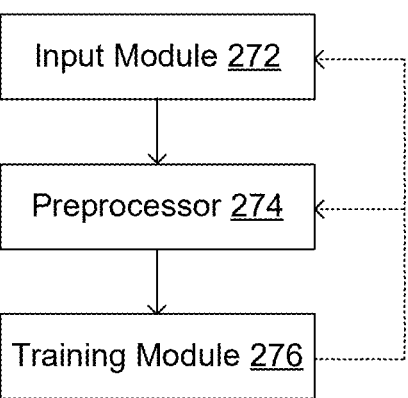
FIG. 2B is a diagram of an example AI architecture in accordance with various aspects described herein.

FIG. 2B is a diagram of an example AI architecture 270 in accordance with various aspects described herein. As shown in FIG. 2B, the AI architecture 270 may include an input module 272, a preprocessor 274, and a training module 276. Some or all of these modules, which may be referred to as programs, processors, or agents, may be realized based on execution of instructions or data by one or more processors of a computing (or ML) system, such as the computing (or ML) system 400 of FIG. 4 (described in more detail below). In various embodiments, the AI architecture 270 may be used to facilitate adjustments to the shape/structure of a wearable IoT device 255 based on sensor data.

The input module 272 may allow for input of (e.g., user-provided) data, such as datasets, parameters, etc., that can be used to train models and/or obtain predictions from models. In some cases, datasets may be labeled and may include inputs (e.g., observed or measured values) and known output data. Labeled datasets may facilitate supervised (or guided) learning. Although not shown, the AI architecture 270 may include a library of ML models or algorithms, such as, for instance, one or more classifiers (e.g., a naïve Bayes classifier or the like), one or more support vector machines, one or more artificial neural networks, one or more learned decision trees, and so on. Each of the ML algorithms may be associated with various parameters.

The preprocessor 274 may be equipped with one or more preprocessing algorithms that are configured to prepare input datasets for processing by the training module 276. Such preprocessing may include discretization (where values are binned or converted into nominal values), component analysis, data estimation, feature selection, feature extraction (e.g., dimensionality reduction, data removal, statistical analysis, threshold-based filtering, etc.), data interpolation, and/or the like.

The training module 276 may be configured to train and evaluate ML models. As an example, the training module 276 may be configured to perform unsupervised learning and/or supervised learning based in input datasets. In exemplary embodiments, the training module 276 may be capable of training and/or evaluating the performance of multiple models in parallel. In one or more implementations, the training module 276 may, despite operating on multiple ML models in parallel, train and evaluate the various ML models individually. In some implementations, the training module 276 may be capable of combining the procedure outcomes of multiple models to derive an aggregate outcome. Model evaluation or validation may involve a comparison of model outputs to known outputs or an analysis of model outputs relative to desired metrics (e.g., relating to performance, disparity, etc.).

Although not shown, the AI architecture 270 may include additional functional modules, such as those for gathering performance results and presenting (e.g., displaying) data regarding the results. While various components, modules, etc. may have been illustrated in FIG. 2B as separate components, modules, etc., it will be appreciated that multiple components, modules, etc. can be implemented as a single component, module, etc., or a single component, module, etc. can be implemented as multiple components, modules, etc. Additionally, functions described as being performed by one component, module, etc. may be performed by multiple components, modules, etc., or functions described as being performed by multiple components, modules, etc. may be performed by a single component, module, etc. In various embodiments, the AI/ML model(s) may be configured to reduce any error in the determinations of adjustments. In this way, any error that may be present may be provided as feedback to the algorithm(s), such that the error may tend to converge toward zero as the algorithm(s) are utilized more and more.

Returning to FIG. 2A, in various embodiments, the adaptive/configurable IoT system 250 may be accessible to health service provider(s) 252 (e.g., via one or more APIs). Health service provider(s) 252 may include physicians or therapists (e.g., chiropractors, physical therapists, etc.) that are registered to utilize the adaptive/configurable IoT system 250 for patient IoT device management. A health service provider 252 may access the adaptive/configurable IoT system 250 using one or more computing devices, such as a desktop computer, a laptop computer, a tablet, a smartphone, etc. As briefly discussed above, the SMO 240 may provide rApp-based slicing functionality, which can facilitate network slicing to support different types of IoT traffic. Service exposure functionality 240e of the SMO 240 may interact with the adaptive/configurable IT system 250 to receive and process IoT-related service requests from health service provider(s) 252, and create appropriate network slices that meet service requirements. Service requirements may identify a health service provider's preferences with respect to latency and/or bandwidth.

Referring now to an example flow shown in FIG. 2A, at reference number 261, sensors of the wearable IoT device 255 may monitor/measure condition(s) and/or position(s) associated with a user's body part(s) and output sensor data. At reference number 262, the wearable IoT device 255 may transmit the data to the adaptive/configurable IoT system 250 via the access network 210 in accordance with provisioned network slices/allocated network resources as facilitated by the AIC 210*i* under instruction by the SMO 240. At reference numbers 263, 264, the adaptive configurable IoT system 250 may, using its AI/ML functionality 250*a* (which may be trained with learnings from treatments for all/other patients), generate treatment instructions/recommendations for reconfiguring the wearable IoT device 255 based on the collected senor data. At reference number 265, a health service provider 252 may have access to collected data, treatments, treatment results, etc. associated with the wearable IoT device 255. At reference numbers 266, 267, the generated treatment instructions/recommendations may be transmitted (e.g., over the core network 220) to the wearable IoT device 255, either by way of the access network 210 or a MEC 210*m*. At reference number 268, the processors in the wearable IoT device 255 may facilitate adjustments by the adjustable component(s) thereof based on the received treatment instructions/recommendations. In an example scenario, a health service provider 252 may have submitted an IoT service request (e.g., in the form of a token) to the SMO 240 via the adaptive/configurable IoT system 250 that includes requirements for service associated with the wearable IoT device 255. In some embodiments, service requirements may include criticality or priority data associated with the wearable IoT device 255 and/or a corresponding user that identifies a level or urgency, such as a need for a higher speed (or lower latency) for communications with the wearable IoT device 255. For instance, a user that is wearing an adaptive shirt for back injury prevention may require more responsive adjustments to be made to the shirt if the user is engaged in heavy lifting activities. In this case, the service requirement may identify a higher priority for the adaptive shirt (e.g., as compared to an adaptive hat for blocking the sun) such that collected sensor data is sent more quickly over the network to the adaptive/configurable IoT system 250 for processing, and treatment instructions/recommendations are sent more quickly back to the adaptive shirt.

In one or more embodiments, the wearable IoT device 255 may (e.g., using its onboard AI/ML functionality) determine adjustments to its shape/structure, but may pass information regarding such determined adjustments to the adaptive/configurable IoT system 250 for suggested changes or approval. In these embodiments, the adaptive/configurable IoT system 250 may analyze the information based on learnings from treatments associated with other users/devices, and determine any refinements to the determined adjustments that might be warranted. For instance, the wearable IoT device 255 may determine an adjustment to a tightness of the device around a user's body part. In this example, the adaptive/configurable IoT system 250 may analyze the proposed adjustment based on learnings from other patients' treatments/results, and determine if any change to the adjustment is needed, such as, for instance, an even tighter adjustment or less tightness. Where the adaptive/configurable IoT system 250 determines that the proposed adjustment is suitable, the adaptive/configurable IoT system 250 may send an approval indication to the wearable IoT device 255. Where the adaptive/configurable IoT system 250 instead determines that a different adjustment is needed, the adaptive/configurable IoT system 250 may send a command regarding the necessary change to the wearable IoT device 255, in which case the wearable IoT device 255 may either override the suggested change or implement it when performing the adjustment. In some embodiments, the wearable IoT device 255 may effect its determined adjustment first in conjunction with requesting the adaptive/configurable IoT system 250 for approval. Upon receiving any necessary change to the adjustment from the adaptive/configurable IoT system 250, the wearable IoT device 255 may then effect the change accordingly. This avoids any delay in treatment that the user receives from the device.

In certain embodiments, the adaptive/configurable IoT system 250 may notify a relevant health service provider 252 regarding proposed adjustments (whether determined by the wearable IoT device 255 or determined by AI/ML functionality associated with the adaptive/configurable IoT system 250) with an option for the health service provider 252 to make any refinements. For example, the adaptive/configurable IoT system 250 may cause information regarding the proposed adjustment to be presented to the health service provider 252 for approval or refinement. In a case where the health service provider 252 determines that the adjustment is suitable, the health service provider 252 may input an approval indication. In a different case where the health service provider 252 determines that the adjustment is not suitable (e.g., based on current recovery progress of the patient, etc.), the health service provider 252 may input a command to change the adjustment, which the adaptive/configurable IoT system 250 may utilize to generate a refinement to the proposed adjustment for forwarding to the wearable IoT device 255.

Now revisiting the AIC 210*i* and the SMO 240, in some embodiments, the AIC 210*i* may assist in the tailoring of IoT services and user experiences. For instance, the AIC 210*i* may (e.g., based on an analysis of the availability, status, etc. of its managed resources and based on the requirements of a requested IoT service) generate suggested or recommended resources to employ in the chain of resources and provide the suggestions to the SMO 240 for consideration as part of IoT service design, orchestration, and resource chaining. In one or more embodiments, the SMO 240 may utilize the abovementioned token in an IoT service request to set policies for the end user device and provision the selected core network 220 with data regarding the wearable IoT device 255, such that when the wearable IoT device 255 attaches to the selected access network 210, the wearable IoT device 255 has the appropriate rights and/or permissions to use the provisioned IoT service. Based on the provisioning, the selected core network 220 may provide the wearable IoT device 255 with information regarding service point connections (e.g., to one or more UPFs or the like in the core infrastructure system architecture).

In one or more embodiments, the SMO 240 may additionally coordinate networking and provisioning of applications and/or services. The SMO 240 may manage transport functions for various layers within the network system 200, and may access application functions for layers above the network system 200. The SMO 240 may provide a platform for network services, network control of service instantiation and management, as well as a programmable environment for resource and traffic management. The SMO 240 may also permit a combination of real-time data transfers for the service and network elements with real-time, or near real-time, control of a forwarding plane. In various embodiments, the SMO 240 may facilitate flow set up in real-time, network programmability, network extensibility, connections via standard interfaces, and/or multi-vendor support. In some embodiments, interactions between layers of the network system 200 can be based upon policies, which can aid in determining an optimal (or best) configuration of the network system 200 as well as aid in rapid adaptation of the network system 200 in response to changing state and changing customer requirements—e.g., predicted demand, addition of new users, spikes in traffic, planned and unplanned network outages, adding new services, and/or maintenance. In certain embodiments, the SMO 240 may also be capable of constructing instances of functions based on requested IoT service needs. For example, in a case where a requested IoT service includes a security attribute, the SMO 240 may construct a firewall (e.g., a dedicated or shared instance) for the requested IoT service.

Although not shown, in various embodiments, the SMO 240 may additionally include a detection and service healing (DSH) element. In various embodiments, the DSH element may monitor the network resources (e.g., for performance, for faults, for QoS purposes (e.g., relating to latency, transmission speed, transmission frequency, routing, the uplink/downlink, QCI, etc.), and/or the like) and provide reports on the network resources (e.g., operational status/health reports or the like) to the SMO 240 to facilitate IoT service design, composition, and orchestration. In one or more embodiments, the DSH element may obtain (e.g., based on the monitoring) information regarding network resource performance and/or faults from the access network resource abstraction layer 230 (for the access network 210) and/or any similar abstraction layers (for a transport network and/or the core network 220).

In some embodiments, the DSH element may obtain fault definitions provided by the SMO 240, which may identify threshold(s) associated with certain data regarding the network resource(s) that the DSH element is to monitor and report on. As an example, a fault definition may include a threshold loading capacity for a network resource, such as a 5G millimeter wave (mmW) access point. In some embodiments, the DSH element may, based on monitoring data regarding a particular network resource, determine whether a parameter of the particular network resource satisfies a threshold (e.g., exceeds the threshold). In a case where the DSH element determines that the parameter satisfies the threshold, the DSH element may provide a corresponding report to the SMO 240, which the SMO 240 may utilize to determine whether the particular network resource should be included in a set of network resources for supporting a requested IoT service. In a case where a service path has already been established by the SMO 240, and where the DSH element determines that a certain network resource, included in the service path, satisfies a certain threshold (which may, for example, relate to an object or requirement of the IoT service), the DSH element may provide a report on performance of the service associated with the certain network resource and/or submit a request to the SMO 240 to repair the IoT service composition or generate a new IoT service composition. In such cases, the SMO 240 may recalculate, or redetermine, an IoT service composition that excludes the non-performant network resource, and cause an adjusted service path to be instantiated. For example, in a case where the SMO 240 determines, based on a report provided by the DSH element that a base station (e.g., in the access network 210) has failed, is overloaded, or is underperforming, and where the SMO 240 identifies an available Wi-Fi access point that a wearable IoT device 255 associated with the IoT service is within communicable range of, the SMO 240 may reinstantiate the service path to exclude the base station and include the Wi-Fi access point. In various embodiments, the SMO 240 may exclude or replace other network resource(s) in a re-determined IoT service composition (e.g., even those network resources that might not be underperforming) if the SMO 240 determines that not doing so might result in system latencies, breaches of rules between the some or all of the network resources in the current IoT service composition, and/or the like.

By providing analytic outputs or the like to the SMO 240, the DSH element enables the SMO 240 to dynamically adjust service paths, and thereby facilitates ongoing, proactive self-management of a IoT service, which improves overall end user experience. Performing load balancing and maximizing use of an entirety of the access network 210 and the core network 220 as part of such self-management can also improve overall network performance. Furthermore, resource abstraction into individual universal resources that are accessible, connectable, and/or stitchable (e.g., based on requested IoT service needs) enables facilitation of IoT services for users.

It is to be appreciated and understood that some or all of the functions described as being performed by a particular device or component of the network system 200 may additionally, or alternatively, be performed by one or more other devices or components of the network system 200. For instance, some or all of the functions described as being performed by the AIC 210*i* may additionally, or alternatively, be performed by the SMO 240, the core network 220, etc. Further, as described above, the SMO 240 may be capable of dynamically altering chains based on detected changes (or trigger conditions). In certain embodiments, the SMO 240 may, subsequent to designing and chaining resources for a given wearable IoT device 255, monitor (e.g., via the AIC 210*i*) the wearable IoT device 255's location (e.g., based on global positioning system (GPS) data, based on data provided by base station(s), and/or the like), and perform additional actions relating to the chaining. For instance, in one or more embodiments, the SMO 244 may, based upon detecting that the wearable IoT device 255 is relocating from an indoor location with high-capacity Wi-Fi network coverage to an outdoor location with only 4G or 5G network coverage, perform one or more actions, such as causing a message to be transmitted to and presented on the wearable IoT device 255 to notify the user of expected performance issues, re-assessing the available network resources to identify any changes that can be made (e.g., selection of a different access network resource, transport network resource, or core network resource, instantiation of a network slice, etc.), and/or the like.

In some embodiments, the AI/ML functionality described herein may be configured to learn treatment instructions/recommendations for adjusting the shape/structure of a wearable IoT device 255. In certain embodiments, the AI/ML functionality may include reinforcement learning (RL) algorithms. For example, in some embodiments, information regarding one or more user treatments (e.g., treatment instructions/recommendations and corresponding treatment results) may be provided as input to an AI/ML model, which may perform learning to automate future treatment instructions/recommendations. For example, the AI/ML model may be trained based on known inputs (e.g., treatments instructions/recommendations, such as, for instance, angling or positioning of one or more components of a shoe insert) and known outputs (e.g., treatment results, such as, for instance, particular improvement in user mobility, decrease in pain level, increase in comfort, etc.). In some embodiments, the AI/ML model may be refined based on feedback received from a user of the wearable IoT device 255 and/or from one or more other devices (e.g., management device(s)). For example, the wearable IoT device 255 and/or one or more other devices may provide feedback indicating whether determined treatment instructions/recommendations made by the machine learning algorithm based on new inputs, helped improve user mobility, decrease pain, increase comfort, etc. When the feedback indicates that a particular determination is useful and/or helpful, the AI/ML model may be trained to make future determinations based on the particular determination (e.g., to determine treatment instructions/recommendations in a manner similar to that in which the particular determination was made). When the feedback indicates that a particular determination is not useful and/or helpful, the AI/ML model may be trained not to make future determinations based on the particular determination (e.g., not to determine treatment instructions/recommendations in a manner similar to that in which the particular determination was made). In this way, the AI/ML functionality can learn how to best determine treatment instructions/recommendations, which improves the accuracy of the determinations, and conserves processor and/or storage resources that may otherwise be used to generate and store rules for determining treatment instructions/recommendations. In various embodiments, the AI or ML functionality may be configured to reduce any error in the determinations of treatment instructions/recommendations. In this way, any error that may be present may be provided as feedback to the algorithm(s), such that the error may tend to converge toward zero as the algorithm(s) are utilized more and more.

It is to be understood and appreciated that, although one or more of FIGS. 1 and 2A might be described above as pertaining to various processes and/or actions that are performed in a particular order, some of these processes and/or actions may occur in different orders and/or concurrently with other processes and/or actions from what is depicted and described above. Moreover, not all of these processes and/or actions may be required to implement the systems and/or methods described herein. Furthermore, while various components, devices, systems, networks, modules, circuits, etc. may have been illustrated in one or more of FIGS. 1 and 2A as separate components, devices, systems, networks, modules, circuits, etc., it will be appreciated that multiple components, devices, systems, networks, modules, circuits, etc. can be implemented as a single component, device, system, network, module, circuit, etc., or a single component, device, system, network, module, circuit, etc. can be implemented as multiple components, devices, systems, networks, modules, circuits, etc. Additionally, functions described as being performed by one component, device, system, network, module, circuit, etc. may be performed by multiple components, devices, systems, networks, modules, circuits, etc., or functions described as being performed by multiple components, devices, systems, networks, modules, circuits, etc. may be performed by a single component, device, system, network, module, circuit, etc.

FIG. 2C depicts an illustrative embodiment of a method 280 in accordance with various aspects described herein. In some embodiments, one or more process blocks of FIG. 2C can be performed by a wearable IoT device, such as the wearable IoT device 255.

At 280a, the method can include obtaining sensor data relating to a body part of a user. For example, the wearable IoT device 255 can, similar to that described above with respect to the system 200 of FIG. 2A, perform one or more operations that include obtaining sensor data relating to a body part of a user.

At 280b, the method can include determining one or more adjustments to a shape or a structure of the device based on the sensor data, resulting in one or more determined adjustments. For example, the wearable IoT device 255 can, similar to that described above with respect to the system 200 of FIG. 2A, perform one or more operations that include determining one or more adjustments to a shape or a structure of the device based on the sensor data, resulting in one or more determined adjustments.

At 280c, the method can include causing the one or more determined adjustments to be made to the shape or the structure of the device, thereby providing for dynamic reconfiguration of the device for facilitating user treatment. For example, the wearable IoT device 255 can, similar to that described above with respect to the system 200 of FIG. 2A, perform one or more operations that include causing the one or more determined adjustments to be made to the shape or the structure of the device, thereby providing for dynamic reconfiguration of the device for facilitating user treatment.

While for purposes of simplicity of explanation, the respective processes are shown and described as a series of blocks in FIG. 2C, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

FIG. 2D depicts an illustrative embodiment of a method 290 in accordance with various aspects described herein. In some embodiments, one or more process blocks of FIG. 2D can be performed by an adaptive/configurable IoT system, such as the adaptive/configurable IoT system 250.

At 290a, the method can include receiving, from a wearable Internet-Of-Things (IoT) device, sensor information relating to a body part of a user, wherein the wearable IoT device is coupled to the body part. For example, the adaptive/configurable IoT system 250 can, similar to that described above with respect to the system 200 of FIG. 2A, perform one or more operations that include receiving, from a wearable Internet-Of-Things (IoT) device, sensor information relating to a body part of a user, wherein the wearable IoT device is coupled to the body part.

At 290b, the method can include generating data regarding one or more adjustments that are to be made to a shape or a structure of the wearable IoT device based on the sensor information. For example, the adaptive/configurable IoT system 250 can, similar to that described above with respect to the system 200 of FIG. 2A, perform one or more operations that include generating data regarding one or more adjustments that are to be made to a shape or a structure of the wearable IoT device based on the sensor information.

At 290c, the method can include causing the data to be transmitted to the wearable IoT device, thereby facilitating dynamic reconfiguration of the wearable IoT device for user treatment. For example, the adaptive/configurable IoT system 250 can, similar to that described above with respect to the system 200 of FIG. 2A, perform one or more operations that include causing the data to be transmitted to the wearable IoT device, thereby facilitating dynamic reconfiguration of the wearable IoT device for user treatment.

While for purposes of simplicity of explanation, the respective processes are shown and described as a series of blocks in FIG. 2D, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 3:
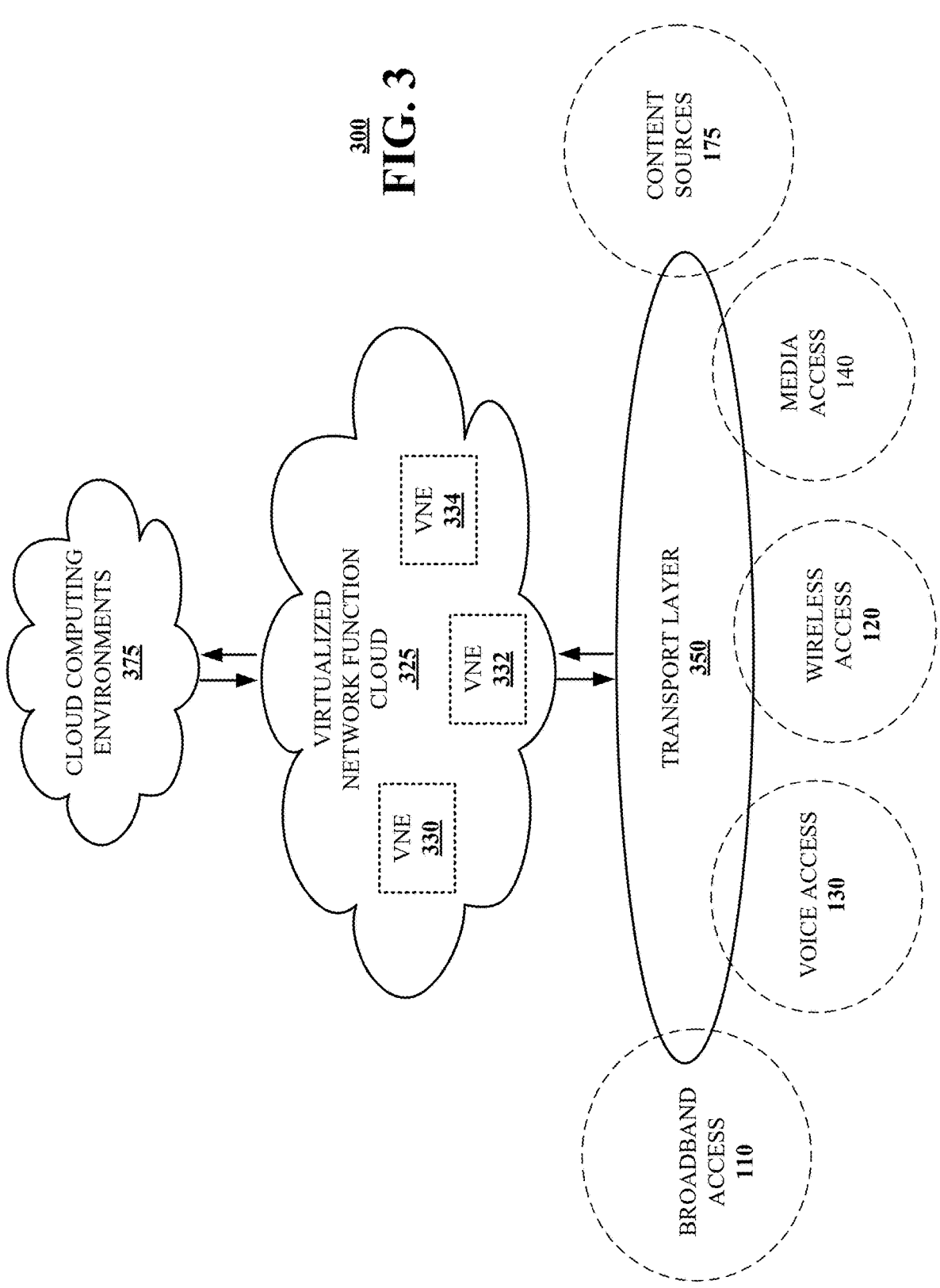
FIG. 3 is a block diagram illustrating an example, non-limiting embodiment of a virtualized communications network in accordance with various aspects described herein.

Referring now to FIG. 3, a block diagram 300 is shown illustrating an example, non-limiting embodiment of a virtualized communications network in accordance with various aspects described herein. In particular, a virtualized communications network is presented that can be used to implement some or all of the subsystems and functions of system 100, the subsystems and functions of system 200, the subsystems and functions of architecture 270, and method 280 presented in FIGS. 1, 2A, 2B, and 2C. For example, virtualized communications network 300 can facilitate, in whole or in part, AI-/ML-enabled adaptive/configurable IoT services for wearable IoT devices.

In particular, a cloud networking architecture is shown that leverages cloud technologies and supports rapid innovation and scalability via a transport layer 350, a virtualized network function cloud 325 and/or one or more cloud computing environments 375. In various embodiments, this cloud networking architecture is an open architecture that leverages application programming interfaces (APIs); reduces complexity from services and operations; supports more nimble business models; and rapidly and seamlessly scales to meet evolving customer requirements including traffic growth, diversity of traffic types, and diversity of performance and reliability expectations.

In contrast to traditional network elements-which are typically integrated to perform a single function, the virtualized communications network employs virtual network elements (VNEs) 330, 332, 334, etc. that perform some or all of the functions of network elements 150, 152, 154, 156, etc. For example, the network architecture can provide a substrate of networking capability, often called Network Function Virtualization Infrastructure (NFVI) or simply infrastructure that is capable of being directed with software and Software Defined Networking (SDN) protocols to perform a broad variety of network functions and services. This infrastructure can include several types of substrates. The most typical type of substrate being servers that support Network Function Virtualization (NFV), followed by packet forwarding capabilities based on generic computing resources, with specialized network technologies brought to bear when general-purpose processors or general-purpose integrated circuit devices offered by merchants (referred to herein as merchant silicon) are not appropriate. In this case, communication services can be implemented as cloud-centric workloads.

As an example, a traditional network element 150 (shown in FIG. 1), such as an edge router can be implemented via a VNE 330 composed of NFV software modules, merchant silicon, and associated controllers. The software can be written so that increasing workload consumes incremental resources from a common resource pool, and moreover so that it is elastic: so, the resources are only consumed when needed. In a similar fashion, other network elements such as other routers, switches, edge caches, and middle-boxes are instantiated from the common resource pool. Such sharing of infrastructure across a broad set of uses makes planning and growing infrastructure easier to manage.

In an embodiment, the transport layer 350 includes fiber, cable, wired and/or wireless transport elements, network elements and interfaces to provide broadband access 110, wireless access 120, voice access 130, media access 140 and/or access to content sources 175 for distribution of content to any or all of the access technologies. In particular, in some cases a network element needs to be positioned at a specific place, and this allows for less sharing of common infrastructure. Other times, the network elements have specific physical layer adapters that cannot be abstracted or virtualized, and might require special DSP code and analog front-ends (AFEs) that do not lend themselves to implementation as VNEs 330, 332 or 334. These network elements can be included in transport layer 350.

The virtualized network function cloud 325 interfaces with the transport layer 350 to provide the VNEs 330, 332, 334, etc. to provide specific NFVs. In particular, the virtualized network function cloud 325 leverages cloud operations, applications, and architectures to support networking workloads. The virtualized network elements 330, 332 and 334 can employ network function software that provides either a one-for-one mapping of traditional network element function or alternately some combination of network functions designed for cloud computing. For example, VNEs 330, 332 and 334 can include route reflectors, domain name system (DNS) servers, and dynamic host configuration protocol (DHCP) servers, system architecture evolution (SAE) and/or mobility management entity (MME) gateways, broadband network gateways, IP edge routers for IP-VPN, Ethernet and other services, load balancers, distributers and other network elements. Because these elements do not typically need to forward substantial amounts of traffic, their workload can be distributed across a number of servers—each of which adds a portion of the capability, and which creates an overall elastic function with higher availability than its former monolithic version. These virtual network elements 330, 332, 334, etc. can be instantiated and managed using an orchestration approach similar to those used in cloud compute services.

The cloud computing environments 375 can interface with the virtualized network function cloud 325 via APIs that expose functional capabilities of the VNEs 330, 332, 334, etc. to provide the flexible and expanded capabilities to the virtualized network function cloud 325. In particular, network workloads may have applications distributed across the virtualized network function cloud 325 and cloud computing environment 375 and in the commercial cloud, or might simply orchestrate workloads supported entirely in NFV infrastructure from these third party locations.

Figure 4:
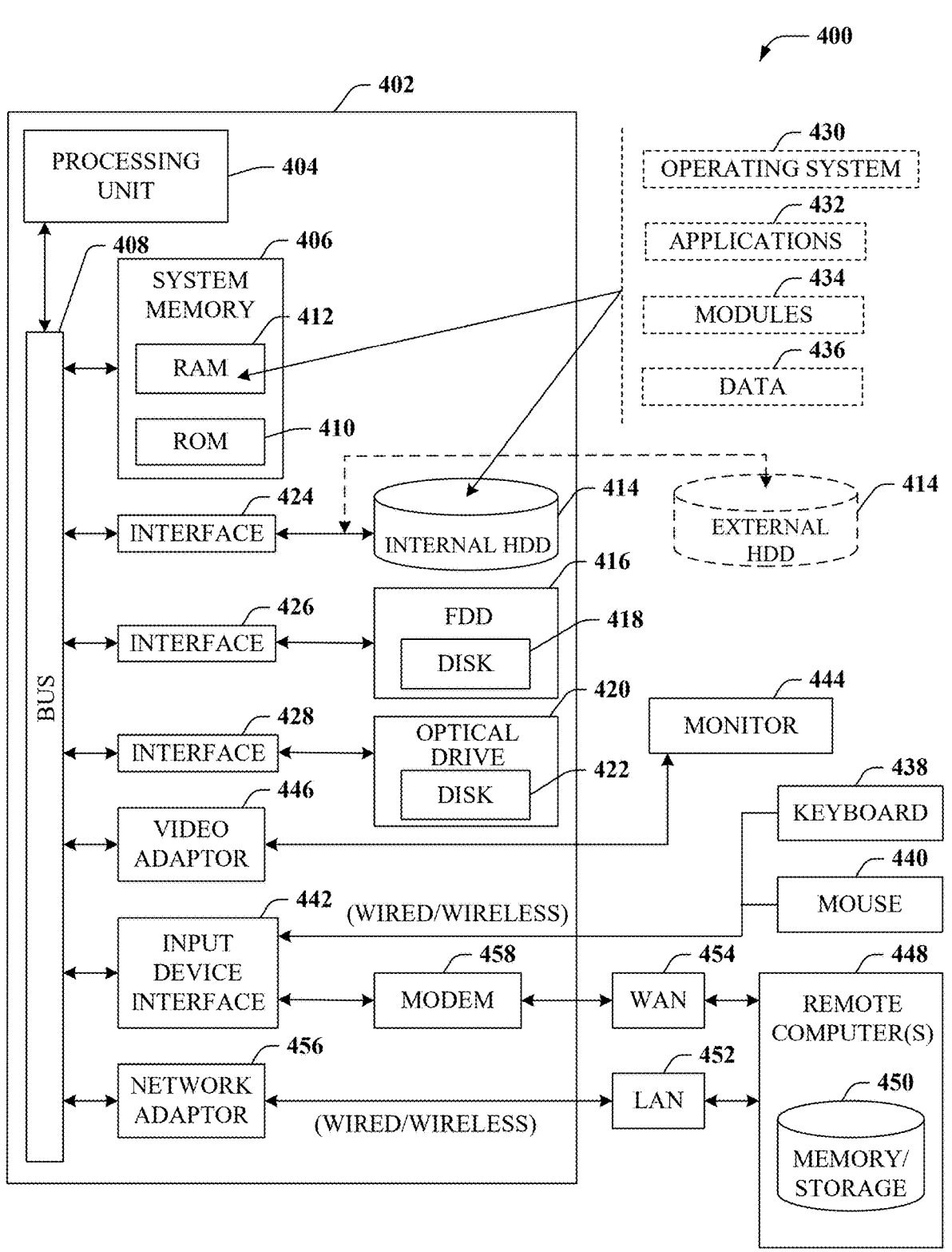
FIG. 4 is a block diagram of an example, non-limiting embodiment of a computing environment in accordance with various aspects described herein.

Turning now to FIG. 4, there is illustrated a block diagram of a computing environment in accordance with various aspects described herein. In order to provide additional context for various embodiments of the embodiments described herein, FIG. 4 and the following discussion are intended to provide a brief, general description of a suitable computing environment 400 in which the various embodiments of the subject disclosure can be implemented. In particular, computing environment 400 can be used in the implementation of network elements 150, 152, 154, 156, access terminal 112, base station or access point 122, switching device 132, media terminal 142, and/or VNEs 330, 332, 334, etc. Each of these devices can be implemented via computer-executable instructions that can run on one or more computers, and/or in combination with other program modules and/or as a combination of hardware and software. For example, computing environment 400 can facilitate, in whole or in part, AI-/ML-enabled adaptive/configurable IoT services for wearable IoT devices.

Generally, program modules comprise routines, programs, components, data structures, etc., that perform particular tasks or implement particular abstract data types. Moreover, those skilled in the art will appreciate that the methods can be practiced with other computer system configurations, comprising single-processor or multiprocessor computer systems, minicomputers, mainframe computers, as well as personal computers, hand-held computing devices, microprocessor-based or programmable consumer electronics, and the like, each of which can be operatively coupled to one or more associated devices.

As used herein, a processing circuit includes one or more processors as well as other application specific circuits such as an application specific integrated circuit, digital logic circuit, state machine, programmable gate array or other circuit that processes input signals or data and that produces output signals or data in response thereto. It should be noted that while any functions and features described herein in association with the operation of a processor could likewise be performed by a processing circuit.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically comprise a variety of media, which can comprise computer-readable storage media and/or communications media, which two terms are used herein differently from one another as follows. Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can comprise, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage or other magnetic storage devices or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

With reference again to FIG. 4, the example environment can comprise a computer 402, the computer 402 comprising a processing unit 404, a system memory 406 and a system bus 408. The system bus 408 couples system components including, but not limited to, the system memory 406 to the processing unit 404. The processing unit 404 can be any of various commercially available processors. Dual microprocessors and other multiprocessor architectures can also be employed as the processing unit 404.

The system bus 408 can be any of several types of bus structure that can further interconnect to a memory bus (with or without a memory controller), a peripheral bus, and a local bus using any of a variety of commercially available bus architectures. The system memory 406 comprises ROM 410 and RAM 412. A basic input/output system (BIOS) can be stored in a non-volatile memory such as ROM, erasable programmable read only memory (EPROM), EEPROM, which BIOS contains the basic routines that help to transfer information between elements within the computer 402, such as during startup. The RAM 412 can also comprise a high-speed RAM such as static RAM for caching data.

The computer 402 further comprises an internal hard disk drive (HDD) 414 (e.g., EIDE, SATA), which internal HDD 414 can also be configured for external use in a suitable chassis (not shown), a magnetic floppy disk drive (FDD) 416, (e.g., to read from or write to a removable diskette 418) and an optical disk drive 420, (e.g., reading a CD-ROM disk 422 or, to read from or write to other high capacity optical media such as the DVD). The HDD 414, magnetic FDD 416 and optical disk drive 420 can be connected to the system bus 408 by a hard disk drive interface 424, a magnetic disk drive interface 426 and an optical drive interface 428, respectively. The hard disk drive interface 424 for external drive implementations comprises at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 402, the drives and storage media accommodate the storage of any data in a suitable digital format. Although the description of computer-readable storage media above refers to a hard disk drive (HDD), a removable magnetic diskette, and a removable optical media such as a CD or DVD, it should be appreciated by those skilled in the art that other types of storage media which are readable by a computer, such as zip drives, magnetic cassettes, flash memory cards, cartridges, and the like, can also be used in the example operating environment, and further, that any such storage media can contain computer-executable instructions for performing the methods described herein.

A number of program modules can be stored in the drives and RAM 412, comprising an operating system 430, one or more application programs 432, other program modules 434 and program data 436. All or portions of the operating system, applications, modules, and/or data can also be cached in the RAM 412. The systems and methods described herein can be implemented utilizing various commercially available operating systems or combinations of operating systems.

A user can enter commands and information into the computer 402 through one or more wired/wireless input devices, e.g., a keyboard 438 and a pointing device, such as a mouse 440. Other input devices (not shown) can comprise a microphone, an infrared (IR) remote control, a joystick, a game pad, a stylus pen, touch screen or the like. These and other input devices are often connected to the processing unit 404 through an input device interface 442 that can be coupled to the system bus 408, but can be connected by other interfaces, such as a parallel port, an IEEE 1394 serial port, a game port, a universal serial bus (USB) port, an IR interface, etc.

A monitor 444 or other type of display device can be also connected to the system bus 408 via an interface, such as a video adapter 446. It will also be appreciated that in alternative embodiments, a monitor 444 can also be any display device (e.g., another computer having a display, a smart phone, a tablet computer, etc.) for receiving display information associated with computer 402 via any communication means, including via the Internet and cloud-based networks. In addition to the monitor 444, a computer typically comprises other peripheral output devices (not shown), such as speakers, printers, etc.

The computer 402 can operate in a networked environment using logical connections via wired and/or wireless communications to one or more remote computers, such as a remote computer(s) 448. The remote computer(s) 448 can be a workstation, a server computer, a router, a personal computer, portable computer, microprocessor-based entertainment appliance, a peer device or other common network node, and typically comprises many or all of the elements described relative to the computer 402, although, for purposes of brevity, only a remote memory/storage device 450 is illustrated. The logical connections depicted comprise wired/wireless connectivity to a local area network (LAN) 452 and/or larger networks, e.g., a wide area network (WAN) 454. Such LAN and WAN networking environments are commonplace in offices and companies, and facilitate enterprise-wide computer networks, such as intranets, all of which can connect to a global communications network, e.g., the Internet.

When used in a LAN networking environment, the computer 402 can be connected to the LAN 452 through a wired and/or wireless communications network interface or adapter 456. The adapter 456 can facilitate wired or wireless communication to the LAN 452, which can also comprise a wireless AP disposed thereon for communicating with the adapter 456.

When used in a WAN networking environment, the computer 402 can comprise a modem 458 or can be connected to a communications server on the WAN 454 or has other means for establishing communications over the WAN 454, such as by way of the Internet. The modem 458, which can be internal or external and a wired or wireless device, can be connected to the system bus 408 via the input device interface 442. In a networked environment, program modules depicted relative to the computer 402 or portions thereof, can be stored in the remote memory/storage device 450. It will be appreciated that the network connections shown are example and other means of establishing a communications link between the computers can be used.

The computer 402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can comprise Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, ag, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands for example or with products that contain both bands (dual band), so the networks can provide real-world performance similar to the basic 10BaseT wired Ethernet networks used in many offices.

Figure 5:
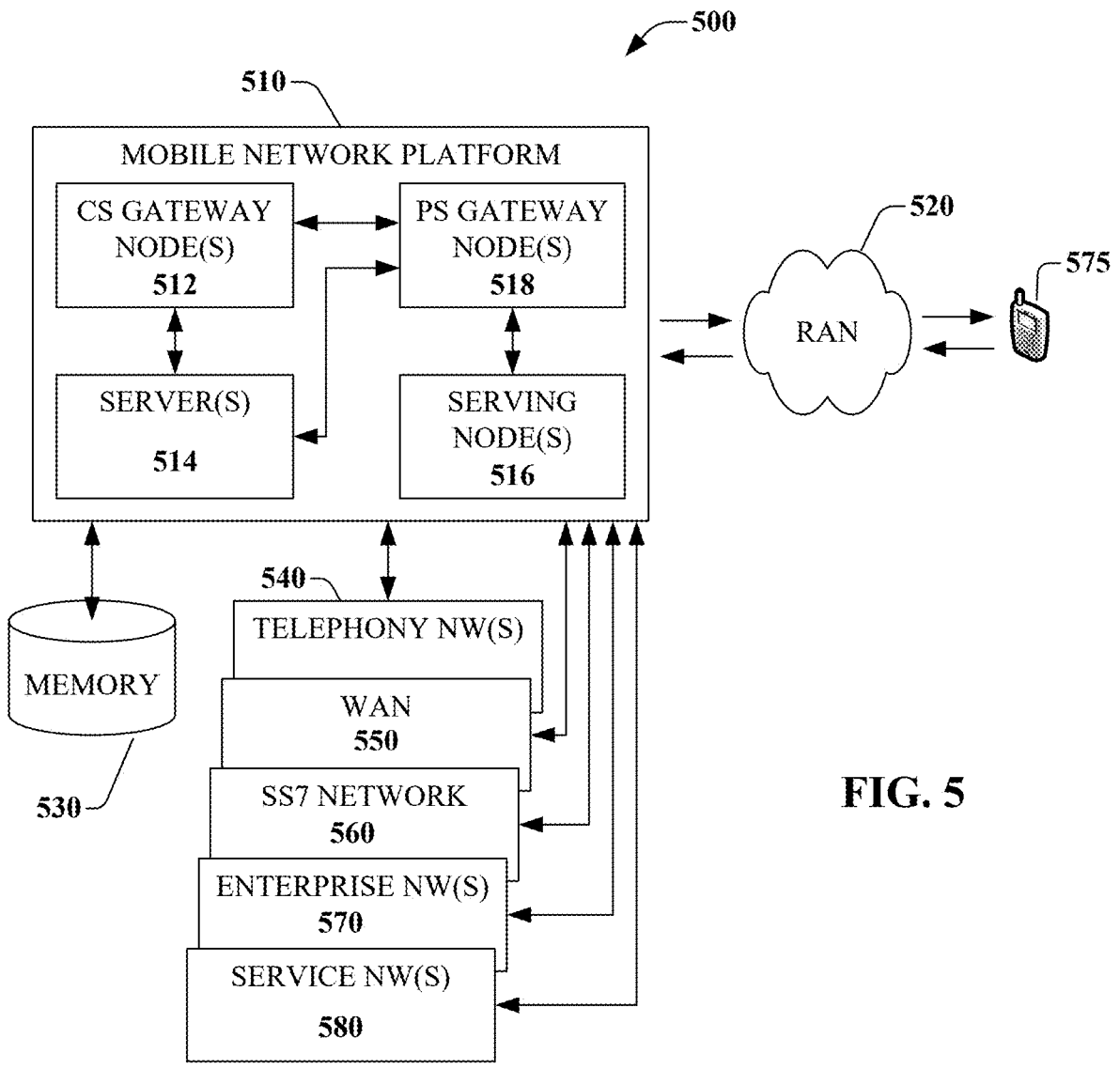
FIG. 5 is a block diagram of an example, non-limiting embodiment of a mobile network platform in accordance with various aspects described herein.

Turning now to FIG. 5, an embodiment 500 of a mobile network platform 510 is shown that is an example of network elements 150, 152, 154, 156, and/or VNEs 330, 332, 334, etc. For example, platform 510 can facilitate, in whole or in part, AI-/ML-enabled adaptive/configurable IoT services for wearable IoT devices. In one or more embodiments, the mobile network platform 510 can generate and receive signals transmitted and received by base stations or access points such as base station or access point 122. Generally, mobile network platform 510 can comprise components, e.g., nodes, gateways, interfaces, servers, or disparate platforms, which facilitate both packet-switched (PS) (e.g., internet protocol (IP), frame relay, asynchronous transfer mode (ATM)) and circuit-switched (CS) traffic (e.g., voice and data), as well as control generation for networked wireless telecommunication. As a non-limiting example, mobile network platform 510 can be included in telecommunications carrier networks, and can be considered carrier-side components as discussed elsewhere herein. Mobile network platform 510 comprises CS gateway node(s) 512 which can interface CS traffic received from legacy networks like telephony network(s) 540 (e.g., public switched telephone network (PSTN), or public land mobile network (PLMN)) or a signaling system #7 (SS7) network 560. CS gateway node(s) 512 can authorize and authenticate traffic (e.g., voice) arising from such networks. Additionally, CS gateway node(s) 512 can access mobility, or roaming, data generated through SS7 network 560; for instance, mobility data stored in a visited location register (VLR), which can reside in memory 530. Moreover, CS gateway node(s) 512 interfaces CS-based traffic and signaling and PS gateway node(s) 518. As an example, in a 3GPP UMTS network, CS gateway node(s) 512 can be realized at least in part in gateway GPRS support node(s) (GGSN). It should be appreciated that functionality and specific operation of CS gateway node(s) 512, PS gateway node(s) 518, and serving node(s) 516, is provided and dictated by radio technology (ies) utilized by mobile network platform 510 for telecommunication over a radio access network 520 with other devices, such as a radiotelephone 575.

In addition to receiving and processing CS-switched traffic and signaling, PS gateway node(s) 518 can authorize and authenticate PS-based data sessions with served mobile devices. Data sessions can comprise traffic, or content(s), exchanged with networks external to the mobile network platform 510, like wide area network(s) (WANs) 550, enterprise network(s) 570, and service network(s) 580, which can be embodied in local area network(s) (LANs), can also be interfaced with mobile network platform 510 through PS gateway node(s) 518. It is to be noted that WANs 550 and enterprise network(s) 570 can embody, at least in part, a service network(s) like IP multimedia subsystem (IMS). Based on radio technology layer(s) available in technology resource(s) or radio access network 520, PS gateway node(s) 518 can generate packet data protocol contexts when a data session is established; other data structures that facilitate routing of packetized data also can be generated. To that end, in an aspect, PS gateway node(s) 518 can comprise a tunnel interface (e.g., tunnel termination gateway (TTG) in 3GPP UMTS network(s) (not shown)) which can facilitate packetized communication with disparate wireless network(s), such as Wi-Fi networks.

In embodiment 500, mobile network platform 510 also comprises serving node(s) 516 that, based upon available radio technology layer(s) within technology resource(s) in the radio access network 520, convey the various packetized flows of data streams received through PS gateway node(s) 518. It is to be noted that for technology resource(s) that rely primarily on CS communication, server node(s) can deliver traffic without reliance on PS gateway node(s) 518; for example, server node(s) can embody at least in part a mobile switching center. As an example, in a 3GPP UMTS network, serving node(s) 516 can be embodied in serving GPRS support node(s) (SGSN).

For radio technologies that exploit packetized communication, server(s) 514 in mobile network platform 510 can execute numerous applications that can generate multiple disparate packetized data streams or flows, and manage (e.g., schedule, queue, format . . . ) such flows. Such application(s) can comprise add-on features to standard services (for example, provisioning, billing, customer support . . . ) provided by mobile network platform 510. Data streams (e.g., content(s) that are part of a voice call or data session) can be conveyed to PS gateway node(s) 518 for authorization/authentication and initiation of a data session, and to serving node(s) 516 for communication thereafter. In addition to application server, server(s) 514 can comprise utility server(s), a utility server can comprise a provisioning server, an operations and maintenance server, a security server that can implement at least in part a certificate authority and firewalls as well as other security mechanisms, and the like. In an aspect, security server(s) secure communication served through mobile network platform 510 to ensure network's operation and data integrity in addition to authorization and authentication procedures that CS gateway node(s) 512 and PS gateway node(s) 518 can enact. Moreover, provisioning server(s) can provision services from external network(s) like networks operated by a disparate service provider; for instance, WAN 550 or Global Positioning System (GPS) network(s) (not shown). Provisioning server(s) can also provision coverage through network(s) associated to mobile network platform 510 (e.g., deployed and operated by the same service provider), such as distributed antenna networks that enhance wireless service coverage by providing more network coverage.

It is to be noted that server(s) 514 can comprise one or more processors configured to confer at least in part the functionality of mobile network platform 510. To that end, the one or more processors can execute code instructions stored in memory 530, for example. It should be appreciated that server(s) 514 can comprise a content manager, which operates in substantially the same manner as described hereinbefore.

In example embodiment 500, memory 530 can store information related to operation of mobile network platform 510. Other operational information can comprise provisioning information of mobile devices served through mobile network platform 510, subscriber databases; application intelligence, pricing schemes, e.g., promotional rates, flat-rate programs, couponing campaigns; technical specification(s) consistent with telecommunication protocols for operation of disparate radio, or wireless, technology layers; and so forth. Memory 530 can also store information from at least one of telephony network(s) 540, WAN 550, SS7 network 560, or enterprise network(s) 570. In an aspect, memory 530 can be, for example, accessed as part of a data store component or as a remotely connected memory store.

In order to provide a context for the various aspects of the disclosed subject matter, FIG. 5, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that perform particular tasks and/or implement particular abstract data types.

Figure 6:
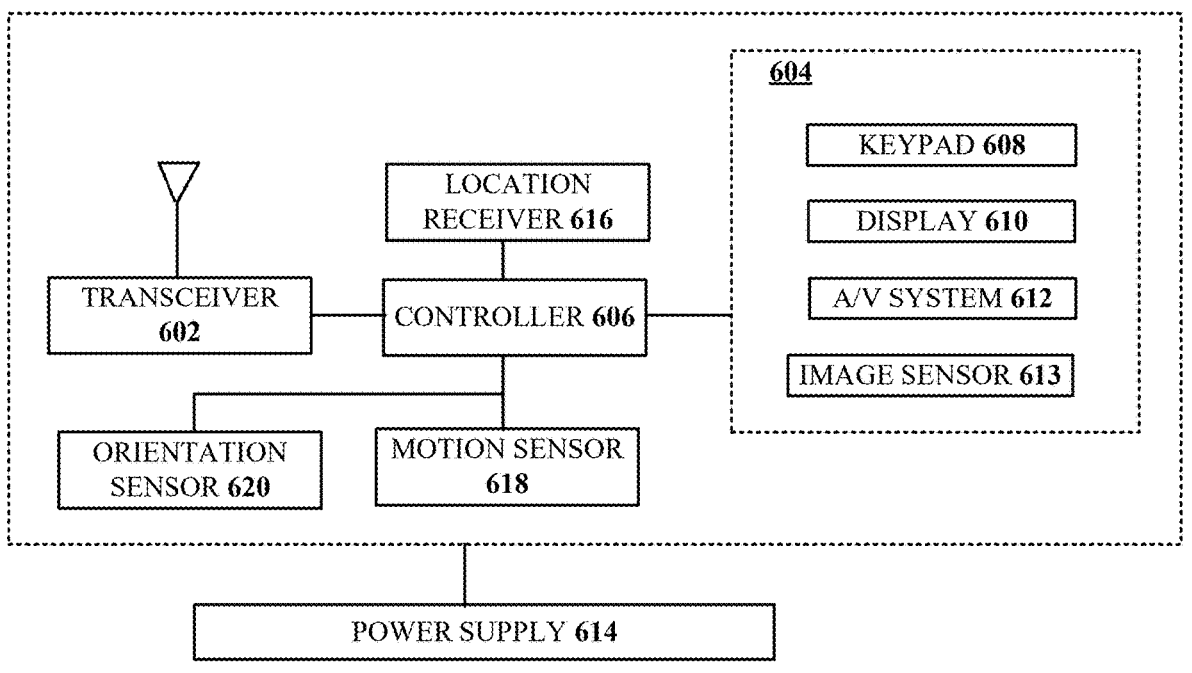
FIG. 6 is a block diagram of an example, non-limiting embodiment of a communication device in accordance with various aspects described herein.

Turning now to FIG. 6, an illustrative embodiment of a communication device 600 is shown. The communication device 600 can serve as an illustrative embodiment of devices such as data terminals 114, mobile devices 124, vehicle 126, display devices 144 or other client devices for communication via communications network 125. For example, computing device 600 can facilitate, in whole or in part, AI-/ML-enabled adaptive/configurable IoT services for wearable IoT devices.

The communication device 600 can comprise a wireline and/or wireless transceiver 602 (herein transceiver 602), a user interface (UI) 604, a power supply 614, a location receiver 616, a motion sensor 618, an orientation sensor 620, and a controller 606 for managing operations thereof. The transceiver 602 can support short-range or long-range wireless access technologies such as Bluetooth®, ZigBee®, Wi-Fi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1×, UMTS/HSDPA, GSM/GPRS, TDMA/EDGE, EV/DO, WiMAX, SDR, LTE, as well as other next generation wireless communication technologies as they arise. The transceiver 602 can also be adapted to support circuit-switched wireline access technologies (such as PSTN), packet-switched wireline access technologies (such as TCP/IP, VOIP, etc.), and combinations thereof.

The UI 604 can include a depressible or touch-sensitive keypad 608 with a navigation mechanism such as a roller ball, a joystick, a mouse, or a navigation disk for manipulating operations of the communication device 600. The keypad 608 can be an integral part of a housing assembly of the communication device 600 or an independent device operably coupled thereto by a tethered wireline interface (such as a USB cable) or a wireless interface supporting for example Bluetooth®. The keypad 608 can represent a numeric keypad commonly used by phones, and/or a QWERTY keypad with alphanumeric keys. The UI 604 can further include a display 610 such as monochrome or color LCD (Liquid Crystal Display), OLED (Organic Light Emitting Diode) or other suitable display technology for conveying images to an end user of the communication device 600. In an embodiment where the display 610 is touch-sensitive, a portion or all of the keypad 608 can be presented by way of the display 610 with navigation features.

The display 610 can use touch screen technology to also serve as a user interface for detecting user input. As a touch screen display, the communication device 600 can be adapted to present a user interface having graphical user interface (GUI) elements that can be selected by a user with a touch of a finger. The display 610 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 610 can be an integral part of the housing assembly of the communication device 600 or an independent device communicatively coupled thereto by a tethered wireline interface (such as a cable) or a wireless interface.

The UI 604 can also include an audio system 612 that utilizes audio technology for conveying low volume audio (such as audio heard in proximity of a human ear) and high volume audio (such as speakerphone for hands free operation). The audio system 612 can further include a microphone for receiving audible signals of an end user. The audio system 612 can also be used for voice recognition applications. The UI 604 can further include an image sensor 613 such as a charged coupled device (CCD) camera for capturing still or moving images.

The power supply 614 can utilize common power management technologies such as replaceable and rechargeable batteries, supply regulation technologies, and/or charging system technologies for supplying energy to the components of the communication device 600 to facilitate long-range or short-range portable communications. Alternatively, or in combination, the charging system can utilize external power sources such as DC power supplied over a physical interface such as a USB port or other suitable tethering technologies.

The location receiver 616 can utilize location technology such as a global positioning system (GPS) receiver capable of assisted GPS for identifying a location of the communication device 600 based on signals generated by a constellation of GPS satellites, which can be used for facilitating location services such as navigation. The motion sensor 618 can utilize motion sensing technology such as an accelerometer, a gyroscope, or other suitable motion sensing technology to detect motion of the communication device 600 in three-dimensional space. The orientation sensor 620 can utilize orientation sensing technology such as a magnetometer to detect the orientation of the communication device 600 (north, south, west, and east, as well as combined orientations in degrees, minutes, or other suitable orientation metrics).

The communication device 600 can use the transceiver 602 to also determine a proximity to a cellular, Wi-Fi, Bluetooth®, or other wireless access points by sensing techniques such as utilizing a received signal strength indicator (RSSI) and/or signal time of arrival (TOA) or time of flight (TOF) measurements. The controller 606 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the communication device 600.

Other components not shown in FIG. 6 can be used in one or more embodiments of the subject disclosure. For instance, the communication device 600 can include a slot for adding or removing an identity module such as a Subscriber Identity Module (SIM) card or Universal Integrated Circuit Card (UICC). SIM or UICC cards can be used for identifying subscriber services, executing programs, storing subscriber data, and so on.

The terms "first," "second," "third," and so forth, as used in the claims, unless otherwise clear by context, is for clarity only and does not otherwise indicate or imply any order in time. For instance, "a first determination," "a second determination," and "a third determination," does not indicate or imply that the first determination is to be made before the second determination, or vice versa, etc.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can comprise both volatile and nonvolatile memory, by way of illustration, and not limitation, volatile memory, non-volatile memory, disk storage, and memory storage. Further, nonvolatile memory can be included in read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, comprising single-processor or multiprocessor computer systems, mini-computing devices, mainframe computers, as well as personal computers, hand-held computing devices (e.g., PDA, phone, smartphone, watch, tablet computers, netbook computers, etc.), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

In one or more embodiments, information regarding use of services can be generated including services being accessed, media consumption history, user preferences, and so forth. This information can be obtained by various methods including user input, detecting types of communications (e.g., video content vs. audio content), analysis of content streams, sampling, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

Some of the embodiments described herein can also employ artificial intelligence (AI) to facilitate automating one or more features described herein. The embodiments (e.g., in connection with automatically identifying acquired cell sites that provide a maximum value/benefit after addition to an existing communications network) can employ various AI-based schemes for conducting various embodiments thereof. Moreover, the classifier can be employed to determine a ranking or priority of each cell site of the acquired network. A classifier is a function that maps an input attribute vector, x=(x1, x2, x3, x4, . . . , xn), to a confidence that the input belongs to a class, that is, f(x) =confidence (class). Such classification can employ a probabilistic and/or statistical-based analysis (e.g., factoring into the analysis utilities and costs) to determine or infer an action that a user desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches comprise, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing UE behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to predetermined criteria which of the acquired cell sites will benefit a maximum number of subscribers and/or which of the acquired cell sites will add minimum value to the existing communications network coverage, etc.

As used in some contexts in this application, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device or computer-readable storage/communications media. For example, computer readable storage media can include, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms such as "user equipment," "mobile station," "mobile," subscriber station," "access terminal," "terminal," "handset," "mobile device" (and/or terms representing similar terminology) can refer to a wireless device utilized by a subscriber or user of a wireless communication service to receive or convey data, control, voice, video, sound, gaming or substantially any data-stream or signaling-stream. The foregoing terms are utilized interchangeably herein and with reference to the related drawings.

Furthermore, the terms "user," "subscriber," "customer," "consumer" and the like are employed interchangeably throughout, unless context warrants particular distinctions among the terms. It should be appreciated that such terms can refer to human entities or automated components supported through artificial intelligence (e.g., a capacity to make inference based, at least, on complex mathematical formalisms), which can provide simulated vision, sound recognition and so forth.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of user equipment. A processor can also be implemented as a combination of computing processing units.

As used herein, terms such as "data storage," data storage," "database," and substantially any other information storage component relevant to operation and functionality of a component, refer to "memory components," or entities embodied in a "memory" or components comprising the memory. It will be appreciated that the memory components or computer-readable storage media, described herein can be either volatile memory or nonvolatile memory or can include both volatile and nonvolatile memory.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

As may also be used herein, the term(s) "operably coupled to," "coupled to," and/or "coupling" includes direct coupling between items and/or indirect coupling between items via one or more intervening items. Such items and intervening items include, but are not limited to, junctions, communication paths, components, circuit elements, circuits, func-tional blocks, and/or devices. As an example of indirect coupling, a signal conveyed from a first item to a second item may be modified by one or more intervening items by modifying the form, nature or format of information in a signal, while one or more elements of the information in the signal are nevertheless conveyed in a manner than can be recognized by the second item. In a further example of indirect coupling, an action in a first item can cause a reaction on the second item, as a result of actions and/or reactions in one or more intervening items.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized. It is also to be understood and appreciated that the subject matter in one or more dependent claims may be combined with that in one or more other dependent claims.

What is claimed is:

1. A device, comprising:

a processing system including a processor; and a memory that stores executable instructions that, when executed by the processing system, facilitate performance of operations, the operations comprising:

obtaining sensor data relating to a body part of a user;

determining one or more adjustments to a shape or a structure of the device based on the sensor data, resulting in one or more determined adjustments, wherein the determining is based on data that is received from a cloud-based server, wherein the device receives services from the cloud-based server via a network slice that is defined by a service management and orchestration system (SMO) of a network in accordance with one or more service level requirements that are provided by a health service provider system specifically for the device, wherein the service level requirements are defined based on a desired responsiveness of treatment for a medical condition associated with the user, wherein the desired responsiveness is selected to prevent injury of the user while the user is engaged in an activity that exerts the body part, and wherein the desired responsiveness is faster compared to a different desired responsiveness for another device that is worn by another user being treated for another medical condition; and causing the one or more determined adjustments to be made to the shape or the structure of the device, thereby providing for dynamic reconfiguration of the device for facilitating user treatment.

2. The device of claim 1, wherein the device comprises a wearable Internet-Of-Things (IoT) device.

3. The device of claim 1, further comprising one or more sensors and one or more adjustable components, and wherein the one or more sensors derive the sensor data based on sensing of a position or a state of the one or more adjustable components, a position or a state of the body part of the user, or a combination thereof.

4. The device of claim 1, wherein the determining is performed using one or more artificial intelligence (AI) algorithms that are implemented in the device.

5. The device of claim 1, wherein the determining is performed using one or more artificial intelligence (AI) algorithms that are implemented in the cloud-based server.

6. The device of claim 5, wherein the one or more AI algorithms are trained based on information regarding a plurality of users.

7. The device of claim 6, wherein the cloud-based server comprises an adaptive Internet-Of-Things (IoT) system that enables one or more health service providers to submit IoT service requests relating to wearable IoT devices.

8. The device of claim 1, wherein the operations further comprise receiving information regarding the one or more adjustments from the cloud-based server via the network slice.

9. The device of claim 1, wherein the desired responsiveness is slower compared to a third desired responsiveness for a third device that is worn by a third user being treated for a third medical condition.

10. The device of claim 8, wherein a service delivery path relating to the network slice includes a mobile edge computing (MEC) device.

11. The device of claim 8, wherein the network slice is facilitated by an access intelligent controller (AIC).

12. A non-transitory machine-readable medium, comprising executable instructions that, when executed by a processing system including a processor, facilitate performance of operations, the operations comprising:

receiving, from a wearable Internet-Of-Things (IoT) device, sensor information relating to a body part of a user, wherein the wearable IoT device is coupled to the body part;

generating data regarding one or more adjustments that are to be made to a shape or a structure of the wearable IoT device based on the sensor information; and causing the data to be transmitted to the wearable IoT device, thereby facilitating dynamic reconfiguration of the wearable IoT device for user treatment, wherein the processing system communicates with the wearable IoT device via a network slice that is defined by a service management and orchestration system (SMO) of a network in accordance with one or more service level requirements that are provided by a health service provider system specifically for the wearable IoT device, wherein the service level requirements are defined based on a desired responsiveness of treatment for a medical condition associated with the user, wherein the desired responsiveness is selected to prevent injury of the user while the user is engaged in an activity that exerts the body part, and wherein the desired responsiveness is faster compared to a different desired responsiveness for another wearable IoT device that is worn by another user being treated for another medical condition.

13. The non-transitory machine-readable medium of claim 12, wherein the processing system comprises an adaptive Internet-Of-Things (IoT) system that enables one or more health service providers to submit IoT service requests relating to wearable IoT devices.

14. The non-transitory machine-readable medium of claim 12, wherein the processing system includes or has access to one or more artificial intelligence (AI) algorithms.

15. The non-transitory machine-readable medium of claim 14, wherein the one or more AI algorithms are implemented in a cloud-based server.

16. The non-transitory machine-readable medium of claim 12, wherein the desired responsiveness is slower compared to a third desired responsiveness for a third wearable IoT device that is worn by a third user being treated for a third medical condition.

17. A method, comprising:

obtaining, by a processing system of a wearable Internet-Of-Things (IoT) device including a processor, sensor data relating to one or more body parts of a user;

determining, by the processing system, one or more adjustments to a shape or a structure of the wearable IoT device based on the sensor data, resulting in one or more determined adjustments, wherein the determining is based on data that is received from a cloud-based server, wherein the wearable IoT device receives services from the cloud-based server via a network slice that is defined by a service management and orchestration system (SMO) of a network in accordance with one or more service level requirements that are provided by a health service provider system specifically for the wearable IoT device, wherein the one or more service level requirements are defined based on a desired responsiveness of treatment for a medical condition associated with the user, wherein the desired responsiveness is selected to prevent injury of the user while the user is engaged in an activity that exerts the body part, and wherein the desired responsiveness is faster compared to a different desired responsiveness for another wearable IoT device that is worn by another user being treated for another medical condition; and causing, by the processing system, the one or more determined adjustments to be made to the shape or the structure of the wearable IoT device, thereby providing for dynamic reconfiguration of the wearable IoT device for facilitating user treatment of the one or more body parts.

18. The method of claim 17, wherein the determining is performed using one or more artificial intelligence (AI) algorithms that are implemented in the wearable IoT device or in a cloud-based server.

19. The method of claim 18, wherein the one or more AI algorithms are trained based on information regarding a plurality of users.

20. The method of claim 18, wherein the cloud-based server comprises an adaptive Internet-Of-Things (IoT) system that enables one or more health service providers to submit IoT service requests relating to wearable IoT devices.

* * * * *